(12) United States Patent
Agrawal et al.

(10) Patent No.: US 6,383,752 B1
(45) Date of Patent: May 7, 2002

(54) PSEUDO-CYCLIC OLIGONUCLEOBASES

(75) Inventors: Sudhir Agrawal, Shrewsbury; Ekambar R. Kandimalla, Worcester, both of MA (US)

(73) Assignee: Hybridon, Inc., Cambridge, MA (US)

(*) Notice: Subject to any disclaimer, the term of this patent is extended or adjusted under 35 U.S.C. 154(b) by 0 days.

(21) Appl. No.: 09/540,699

(22) Filed: Mar. 31, 2000

Related U.S. Application Data

(60) Provisional application No. 60/127,538, filed on Mar. 31, 1999, and provisional application No. 60/174,642, filed on Jan. 5, 2000.

(51) Int. Cl.[7] .......................... C12Q 1/68; C07H 21/04; C07H 19/04
(52) U.S. Cl. .......................... 435/6; 536/24.3; 536/26.6
(58) Field of Search .............................. 435/6; 536/23.3, 536/26.6, 24.3

(56) References Cited

FOREIGN PATENT DOCUMENTS

EP          606 889 A2  *  6/1994  ............ C12Q/1/68

* cited by examiner

Primary Examiner—Kenneth R. Horlick
Assistant Examiner—Teresa Strzelecka

(74) Attorney, Agent, or Firm—Hale and Dorr LLP

(57) ABSTRACT

The present invention comprises a new class of oligonucleobases (e.g., oligonucleotides), which we call "pseudo-cyclic oligonucleotides" (PCOs). PCOs contain two oligonucleotide segments attached through their 3'-3' or 5'-5' ends. One of the segments (the "functional segment") of the PCO has some functionality (e.g., an antisense oligonucleotide complementary to a target mRNA). Another segment (the "protective segment") is complementary to the 3'- or 5'-terminal end of the functional segment (depending on the end through which it is attached to the functional segment). As a result of complementarity between the functional and protective segment segments, PCOs form intramolecular pseudo-cyclic structures in the absence of the target nucleic acids (e.g., RNA). PCOs are more stable than conventional antisense oligonucleotides because of the presence of 3'-3' or 5'-5' linkages and the formation of intramolecular pseudo-cyclic structures. Pharmacokinetic, tissue distribution, and stability studies in mice suggest that PCOs have higher in vivo stability than and, pharmacokinetic and tissue distribution profiles similar to, those of PS-oligonucleotides in general, but rapid elimination from selected tissues. When a fluorophore and quencher molecules are appropriately linked to the PCOs of the present invention, the molecule will fluoresce when it is in the linear configuration, but the fluorescence is quenched in the cyclic conformation. Such oligos are useful for diagnostic purposes.

33 Claims, 23 Drawing Sheets

| SEQ. ID.NO. | SEQUENCE[a] | SECONDARY STRUCTURE[b] | $T_m$ (°C) IN THE[c] ABSENCE OF RNA | $T_m$ (°C) IN THE[c] PRESENCE OF RNA |
|---|---|---|---|---|
| 1 | 5'-GCGTGCCTCCTCACTGGC-3' | | – | 67.7 |
| 2 | 3'-CGGTCACTCCTCCGTGCG-5'-5'-GCCAGT-3' | GCCAGT / CGGTCAC_T \ G_C C_GTGCCT C^C | 51.9 | 74.8 |
| 3 | 3'-CGGTCACTCCTCCGTGCG-5'-5'-GC<u>GAA</u>T-3' | GC<u>GAA</u>T / CGGTCAC_T \ G_C C_GTGCCT C^C | bt | 76.3 |
| 4 | 5'-GCGTGCCTCCTCACTGGC-3'-3'-CGCACG-5' | CGCACG / GCGTGCC_T \ C_G G_GTCACT C^C | 56.5 | 76.7 |
| 5 | 5'-GCGTGCCTCCTCACGGC-3'-3'-<u>GGAACC</u>-5' | <u>GGAACC</u> / GCGTG<u>C</u>C_T \ C_G G_GTCACT C^C | bt | 76.8 |
| 6 | 5'-GCGTGCCTCCTCACTGGC-3'-3'-CGCAC-5' | CGCAC / GCGTGCC_T \ C_G G_GTCACT C^C | bt | 66.9 |
| 7 | 5'-GCGTGCCTCCTCACTGGC-3'-3'-CGCACG-5' | CGCACG / GCGTGCC_T \ C_G G_GTCACT C^C | 48.0 | 68.1 |
| 8 | 5'-GCGTGCCTCCTCACTGGC-3'-3'-CGCACGG-5' | CGCACGG / GCGTGCC_T \ C_G G_GTCACT C^C | 50.2 | 67.1 |
| 9 | 5'-GCGTGCCTCCTCACTGGC-3'-3'-CGCACGGA-5' | CGCACGGA / GCGTGCC_T \ C_G G_GTCACT C^C | 55.3 | 67.4 |
| 10 | 5'-GCGTGCCTCCTCACTGGC-3'-3'-<u>GGAAC</u>-5' | <u>GGAAC</u> / GCGTGCC_T \ C_G G_GTCACT C^C | bt | 68.3 |
| 11 | 5'-GCGTGCCTCCTCACTGGC-3'-3'-<u>GGAACAG</u>-5' | <u>GGAACAG</u> / GCGTGTC_T \ C_G G_GTCACT C^C | bt | 68.2 |

[a] BOLD AND PLAIN LETTERS REPRESENT PHOSPHODIESTER (PO) AND PHOSPHOROTHIOATE (PS) LINKAGES, RESPECTIVELY, UNDERLINED BASES REPRESENT MISMATCHES. [b] ⁄⁄ AND ⁄ REPRESENT 5'-5' AND 3'-3' LINKAGES, RESPECTIVELY. [c] SEE EXPERIMENTAL SECTION FOR BUFFER CONDITIONS; bt REPRESENTS BROAD TRANSITION WITHOUT A DEFINED MELTING TEMPERATURE.

FIG. 7

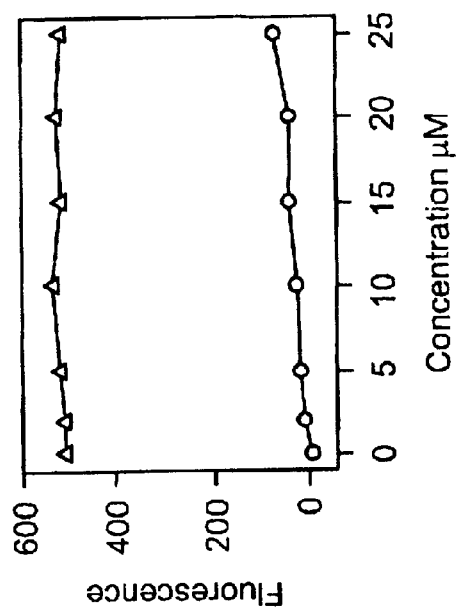
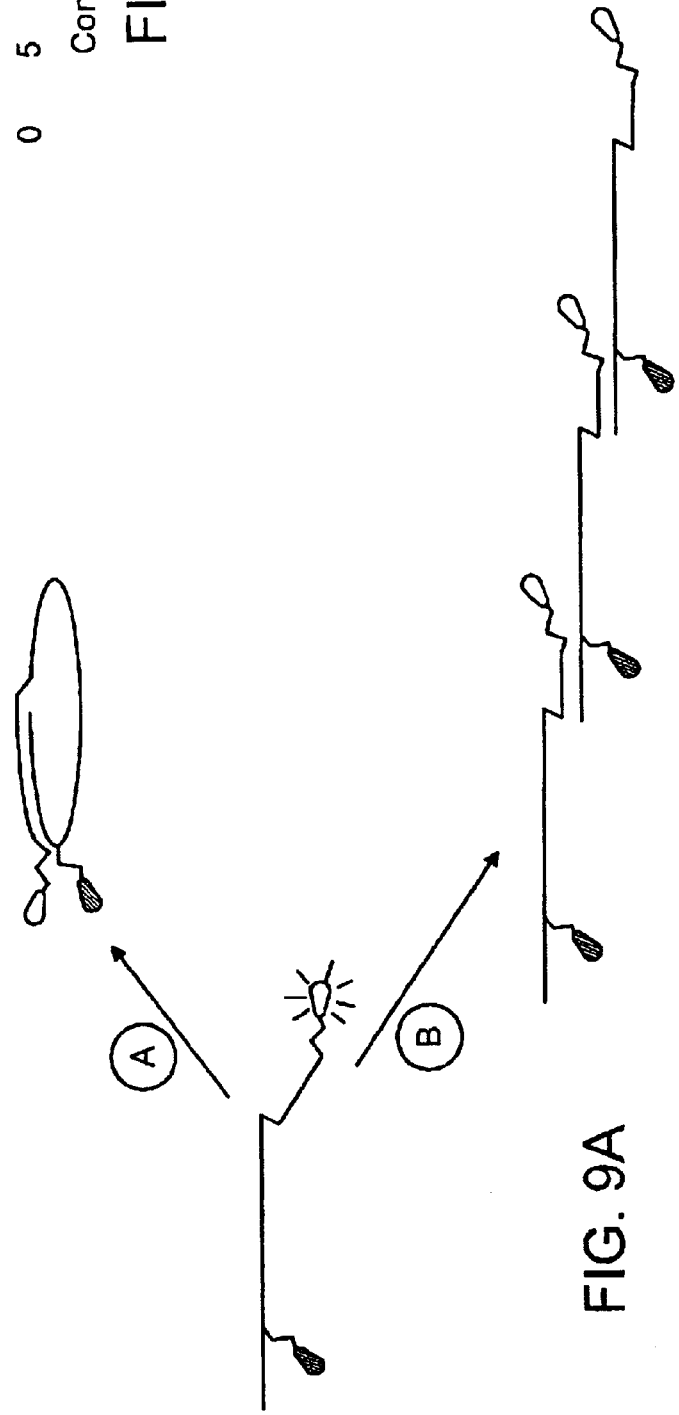
FIG. 9B
FIG. 9A

| Template<br>SEQ. ID. NO. 17 | 3'-TTCCACTGTGGACAAGAGTGAGTGTCTACATGGACCCAGG-5' | |
|---|---|---|
| Primer 2<br>SEQ. ID. NO. 22 | 5'-TGACACCTGTTCTCACTCAC | 36-mer |
| Primer 3<br>SEQ. ID. NO. 23 | 5'-GGTGACACCTGTTCTCACT*C | 38-mer |
| Primer 4<br>SEQ. ID. NO. 24 | 5'-GTGACACCTGTTCTCACT*CA | 37-mer |
| Primer 5<br>SEQ. ID. NO. 25 | 5'-GACACCTGTTCTCACT*CACA | 35-mer |
| Primer 6<br>SEQ. ID. NO. 26 | 5'-CACCTGTTCTCACT*CACAGA | 33-mer |

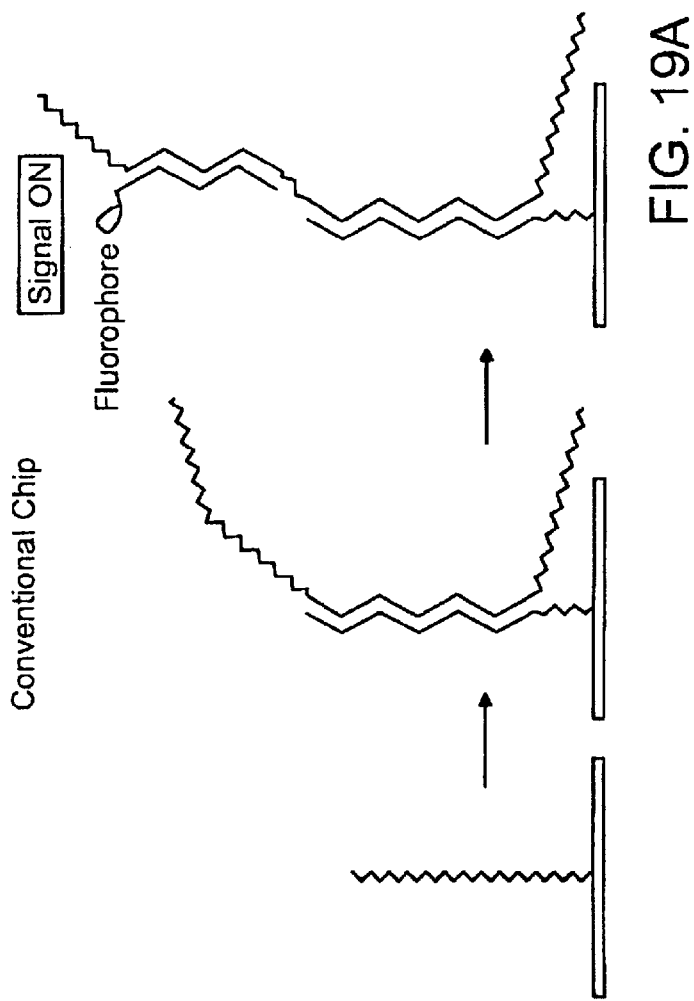
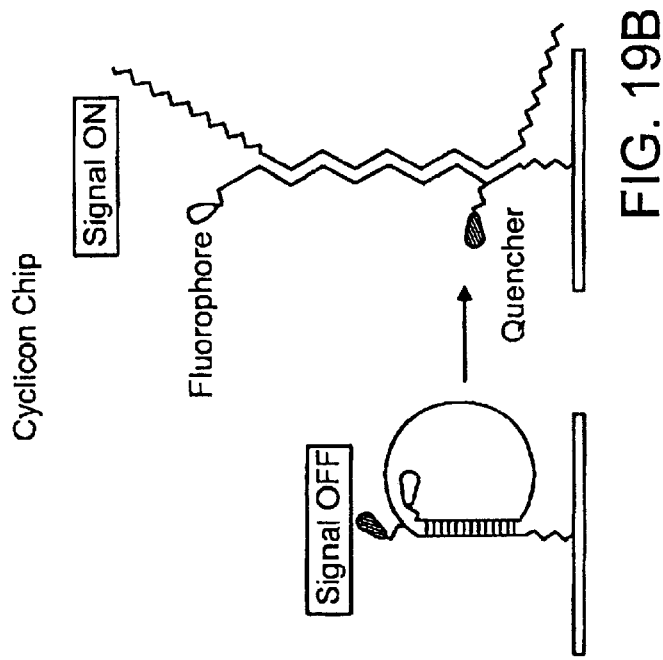
FIG. 19A
FIG. 19B

PSEUDO-CYCLIC OLIGONUCLEOBASES

This application claims the benefit of U.S. Provisional Application No. 60/127,538, filed Mar. 31, 1999, and U.S. Provisional Application No. 60/174,642, filed Jan. 5, 2000.

BACKGROUND OF THE INVENTION

1. Field of the Invention

This invention relates to the field of oligonucleobases, such as oligonucleotides, for general use and possessing a new structural motif that enables the oligonucleobase to reversibly circularize.

2. Summary of the Related Art

Progress in the discovery and development of antisense oligonucleotides as therapeutic agents is continuing at a rapid pace (1–3). For the effective use of an oligonucleotide, it must interact with the target mRNA by Watson-Crick base pairing, activate RNase H for mRNA cleavage, be stable towards nucleases, and be taken up by cells efficiently (4,5). Oligodeoxynucleotide phosphorothioates (PS-oligonucleotides) possess all these properties and have been studied extensively for their in vitro and in vivo biological activity (6–10), safety (3,11–15), and pharmacokinetic profiles (15–19). The potential application of PS-oligonucleotides) as therapeutic agents is currently being evaluated in a number of human clinical trials (2). In order to further improve the potential of PS-oligonucleotides as antisense agents, we have introduced and evaluated various mixed-backbone oligonucleotides (MBOs) (20–24). In MBOs, the desirable properties of PS-oligonucleotides are maintained while undesirable properties are minimized by a combination of modifications in oligonucleotides. MBOs containing 2'-O-alkylribonucleotides have been studied extensively and have yielded promising results in terms of biological activity, in vivo stability, and general toxicity (21,25–27). Based on their advantages over PS-oligonucleotides, MBOs have become the first choice of second-generation antisense oligonucleotides and are currently being studied for their potential in human clinical trials.

In continuation of our efforts to improve the properties of PS-oligonucleotides as therapeutic agents, we have considered structural changes in PS-oligonucleotides. In our earlier studies we reported self-stabilized oligonucleotides, a PS-oligonucleotide containing a hairpin loop region at the 3'-end that provided increased in vivo nuclease stability and improved biological activity, and more importantly improvement in toxicity compared to a PS-oligonucleotide without a secondary structure at the 3'-end (12,28–30). Follow up studies by others have also yielded encouraging results (31).

In recent years, techniques based on the complementary hybridization between oligonucleotides and nucleic acid targets have also been widely applied in molecular diagnostics, therapeutics development, and mechanistic and molecular biological studies. As a result of human genome analysis, these techniques have become routine and there is an ever-increasing demand for more rapid, accurate, and effective nucleic acid detection and measurement methods. Fluorescence-based methods are more rapid and sensitive for hybridization detection and measurement than are the methods based on absorbance spectroscopy, calorimetry, and magnetic resonance spectroscopy. The advantage of the fluorescence-based techniques for monitoring complementary hybridization is that they can be used in both solution and solid-phase applications.

The polymerase-chain reaction (PCR) is extensively used in molecular biological and genetics based research and is increasingly becoming an essential tool for molecular diagnostics. Several homogenous fluorescence assay methods for probing amplification products in PCR reactions have been developed in recent years. These include TaqMan (40,41), molecular beacon (42), hairpin-primer (43), and scorpion (44).

Despite the advances that we and others have made, there is still a desire to develop antisense oligonucleotides having improved properties for use as therapeutic agents and in diagnostic applications.

SUMMARY OF THE INVENTION

The present invention provides a new structural class of oligonucleobases referred to herein as "pseudo-cyclic oligonucleobases" (PCOs) or, equivalently, cyclicons. In PCOs, two oligonucleobases are linked to each other (directly or through a linker segment). One oligonucleobase, called herein the "functional segment," (or, equivalently, the "primer" or "primer-probe" segment) provides functionality to the PCO (e.g., the functional segment can be an antisense oligonucleotide), and the second, called herein the "protective segment" (or, equivalently, the "modifier segment") is complementary to the terminal end of the functional segment (FIG. 1).

Under selected conditions, PCOs adopt an intramolecular cyclic or pseudo-cyclic structure as a result of complementarity between functional and protective segments, which form an intramolecular duplex (FIG. 1). Intramolecular duplex formation protects the functional segment, enhancing its stability. For example, when the functional segment is an antisense oligonucleotide and the functional segment and protective segment are connected via a 3'-3'-linkage, the linkage provides increased nuclease stability against 3'-exonucleolytic attack. The duplex formed between the antisense and protective segments provides additional nuclease stability against 5'-exonucleases.

These designer oligonucleobases may stay in linear form or hybridized form (FIG. 1) depending on the temperature, salt concentration, and length of the protective segment. If the PCO is in the intramolecular pseudo-cyclic form, it may exhibit fewer of the polyanionic-related side effects (e.g., complement activation and prolongation of partial thromboplastin time) known to occur with PS-oligonucleotides, because there are fewer exposed phosphorothioate linkages.

PCOs according to the invention can be made using standard techniques for synthesis of the constituent oligonucleobases and are useful for all purposes for which the functional oligonucleobase is useful.

The foregoing merely summarizes certain aspects of the invention and is not intended, nor should it be construed, as limiting the invention in any manner. All patents, patent applications, and other publications recited in this specification are hereby incorporated by reference in their entirety.

BRIEF DESCRIPTION OF THE DRAWINGS

In FIGS. 6A and 6B no shade, light shaded and dark shaded bars represent tissue disposition of oligonucleotide at 3 hr, 48 hr, and 96 hr, respectively, after administration to mice. The data represent mean±SD from at least two mice.

FIG. 7 displays a table of the oligonucleotides used in the Examples, including their primary and secondary structures and $T_m$s in the presence and absence of target RNA.

FIG. 9A displays intra- (A) and inter-molecular (B) interactions of cyclicons.

FIG. 9B displays fluorescence of oligonucleotide 14 (SEQ. ID NO:14) with increasing concentrations of the same sequence synthesized without fluorophore and quencher tags (O), and the same solution in the presence of a complementary oligodeoxynucleotide strand (Δ).

FIGS. 19A and B present a schematic comparison between conventional detection of a nucleic on a chip and detection of nucleic acids using PCOs of the invention on a chip.

DETAILED DESCRIPTION OF THE INVENTION

Figure 1:
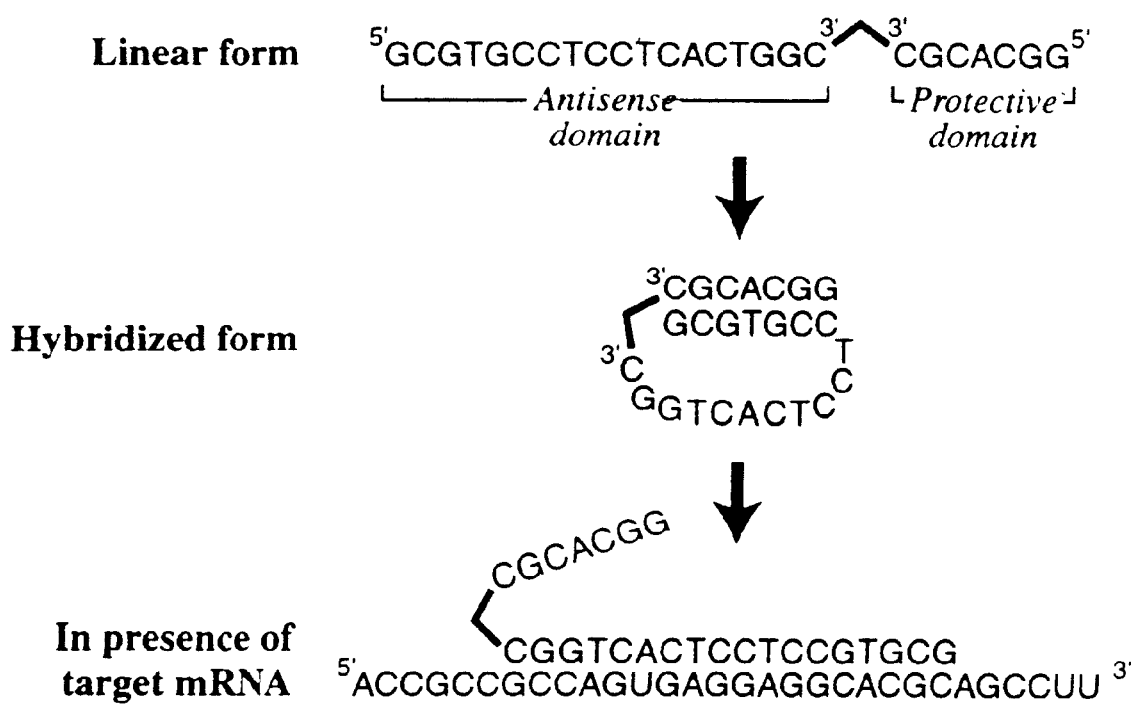
FIG. 1 is a graphical representation of oligonucleobases according to the invention showing two regions of pseudo-cyclic oligonucleotide (PCO)—a functional segment (an antisense oligonucleotide) and a protective segment. In pseudo-cyclic form, the antisense and protective segments of a PCO hybridize to each other. In the presence of a complementary RNA, the PCO adopts a linear form because of the higher stability of the heteroduplex between antisense oligonucleotide and the target RNA.

The present invention provides a new class of oligonucleobases, called pseudo-cyclic oligonucleobases ("PCOs") consisting essentially of a functional segment, a protective segment, and a linker segment, wherein a) the functional segment comprises an oligonucleobase of N nucleobases having a terminal end and a linker end;

b) the protective segment comprises an oligonucleobase of M nucleobases having a terminal end and a linker end and is both complementary to a sequence of nucleobases within the functional segment and of polarity opposite to the sequence of nucleobases in the functional segment to which it is complementary;

c) the functional segment and the protective segment are covalently linked to each other at their linker ends through the linker segment, wherein the linker segment is a direct bond, a mono- or oligonucleobase of K nucleobases, or other chemical moiety;

d) the protective segment and the functional segment form a duplex under selected conditions;

e) N is 11 to 75;
f) M is 5 to 30; and
g) K is 2 to 5.

When the PCO of the invention is employed to hybridize to a target nucleobase (e.g., and mRNA), the functional segment comprises a sequence of nucleobases complementary to the target nucleobase, and the nucleobase sequence of the functional segment comprises 6 or more contiguous nucleobases that are single stranded under the selected conditions. In such embodiments, therefore, the functional segment is at least 6 nucleobases longer than the protective segment (i.e., N−M≧6). In general, the PCO is constructed so the terminal end of the functional segment will form a duplex with the protective segment, i.e., the protective segment is complementary to the terminal end of the functional segment.

The functional segment is an oligonucleobase that performs a desired function, e.g., an antisense oligonucleotide or an aptamer.

As used herein, the term "nucleobase" means any heterocyclic base that has the ability to hydrogen bond with a complementary target. In a preferred embodiment, the nucleobase is a modified or unmodified, synthetic or natural purine or pyrimidine base, e.g. adenine, guanine, cytosine, uridine, thymine, xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-aza uracil, cytosine and thymine, 5-uracil pseudo uracil), 4-thiouracil, 8-halo, amino, thiol, thiolalkyl) hydroxyl and other 8 substituted adenines and guanines, 5-trifluoromethyl and other 5 substituted uracils and cytosines and 7-methylguanine. Other purines and pyrimidines include those disclosed in U.S. Pat. No. 3,687,808, those disclosed in the Concise Encyclopedia Of Polymer Science And Engineering, J. I. Kroschwitz, Ed. John Wiley & Sons, 1990 at pages 858–859 and those disclosed by Englisch, et al., Angewandte Chemie, International Edition 1991, 30, 613. Nucleotides are a preferred nucleobase.

An "oligonucleobase" is a polymer of nucleobases that can hybridize to a complementary target by, for example, Watson-Crick base pairing. Nucleobases of the oligonucleobase can be connected via internucleobase linkages, e.g., peptidyl linkages (as in the case of peptide nucleic acids (PNAs); Nielsen et al. (1991) *Science* 254, 1497 and U.S. Pat. No. 5,539,082) and morpholino linkages (Qin et al., *Antisense Nucleic Acid Drug Dev.* 10, 11 (2000); Summerton, *Antisense Nucleic Acid Drug Dev.* 7, 187 (1997); Summerton et al., *Antisense Nucleic Acid Drug Dev.* 7, 63 (1997); Taylor et al., *J Biol Chem.* 271, 17445 (1996); Partridge et al., *Antisense Nucleic Acid Drug Dev.* 6, 169 (1996)), or by any other natural or modified linkage. The oligonucleobases can also be Locked Nucleic Acids (LNAs). Nielsen et al., *J Biomol Struct Dyn* 17, 175 (1999); Petersen et al., *J Mol Recognit* 13, 44 (2000); Nielsen et al., *Bioconjug Chem* 11, 228 (2000). Oligonucleotides are preferred oligonucleobases.

In a preferred embodiment, the nucleobases are connected via a sugar-phosphate backbone. The sugar moiety can be natural or modified; preferably the sugar moiety is a pentosefuranosyl moiety, which can be ribose, substituted ribose, and 2'-deoxyribose. When the sugar moiety is a ribose, it links adjacent nucleobases via a 3'-5' (preferably) or 2'-5' linkage. Preferred substituted ribose moieties are 2'-O-substituted ribose where the 2'-O substituent comprises a $C_{1-6}$ saturated or unsaturated alkyl (preferably methyl), $C_1$–$C_6$alkoxy$C_1$–$C_6$alkyl (preferably methoxyethyl), or an aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such substituted ribose moieties can be those bearing a 2' substitution with such as an amino or halo group.

The phosphate moiety is a modified or unmodified phosphodiester linkage, including, for example, phosphorothioate (preferably), phosphorodithioate, $C_1$–$C_6$alkylphosphonate, $C_1$–$C_6$alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate, phospholinol, boranophosphate (Shaw et al., *Methods Enzymol.* 313, 226 (2000) Rait et al., *Antisense Nucleic Acid Drug Dev.* 9, 53 (1 999); Porter et al., *Nucleic Acids Res.* 15, 1611 (1997) and sulfone internucleotide linkages. In certain preferred embodiments, these phosphate moiety is a phosphodiester, phosphotriester, phosphorothioate, or phosphoramidate linkages, or combinations thereof. Oligonucleobases according to the invention can comprise any combination of nucleobases and internucleobase linkages.

In many embodiments, intramolecular duplex formation occurs between segments of defined polarity in parallel or anti-parallel fashion. As used herein, the term "polarity" refers to the concept of directionality in primary structure (e.g., 3'→5' and 5'→3' in the case of DNA and RNA, or N-terminal→C-terminal (or visa versa) in the case of PNAs). In the case where the PCOs of the invention comprise oligonucleotides, for example, which hybridize by Watson-Crick base pairing in anti-parallel fashion, the protective segment will be in the 3' (or 2')→5' configuration and the sequence of nucleotides to which it is complementary in the functional segment will be in the 5' to 3' (or 2') configuration, or visa versa. The change in polarity in the PCO can occur anywhere in the PCO other than in the protective segment and the sequence of nucleotides in the functional segment to which the protective segment is complementary. In a preferred embodiment where the PCO comprises oligonucleotides, the functional segment is in the 3'→5' configuration and the protective segment is in the 5'→3' configuration, or visa versa.

Oligonucleobases used in the PCOs of the invention may also have additional substituents, including without limitation lipophilic groups, intercalating agents, biotin, streptavidin, diamines and adamantane. Such substituents may be desired, for example, to enhance cellular uptake. Such moieties include but are not limited to lipid moieties such as a cholesterol moiety, a cholesteryl moiety (Letsinger et al. (1989) *Proc. Natl. Acad. Sci. USA* 86, 6553), cholic acid (Manoharan et al. (1994) *Bioorg. Med. Chem. Let.,* 4, 1053), a thioether, e.g., hexyl-S-tritylthiol (Manoharan et al. (1992) *Ann. N.Y. Acad. Sci.* 660, 306; Manoharan et al. (1993) *Bioorg. Med. Chem. Let.,* 3, 2765), a thiocholesterol (Oberhauser et al. (1992) *Nucl. Acids Res.,* 20, 533), an aliphatic chain, e.g., dodecandiol or undecyl residues (Saison-Behmoaras et al. (1991) *EMBO J.,* 10, 111; Kabanov et al. (1990) *FEBS Lett.,* 259, 327; Svinarchuk et al. (1993) *Biochimie,* 75, 49), a phospholipid, e.g., di-hexadecyl-rac-glycerol or triethylammonium 1,2-di-O-hexadecyl-rac-glycero-3-H-phosphonate (Manoharan et al. (1995) *Tetrahedron Lett.,* 36, 3651; Shea et al. (1990) *Nucl. Acids Res.,* 18, 3777), a polyamine or a polyethylene glycol chain (Manoharan et al. (1995) *Nucleosides & Nucleotides,* 14, 969), or adamantane acetic acid (Manoharan et al. (1995) *Tetrahedron Lett.,* 36, 3651). Oligonucleotides comprising lipophilic moieties, and methods for preparing such oligonucleotides are known in the art, for example, U.S. Pat. Nos. 5,138,045, 5,218,105 and 5,459,255.

As used herein, the term "complementary" refers to a pair of nucleobases that hydrogen bond to each other in preference to other heterocyclic bases under selected (e.g., physiological) conditions. When the nucleobases are modified or unmodified, natural or synthetic purines and pyrimidines, the term "complementary" means complementary in the Watson Crick sense.

In a preferred embodiment, the functional segment and protective segment are oligonucleotides comprised of modified or unmodified deoxyribonucleotides, ribonucleotides, or combinations thereof having phosphodiester linkages, phosphorothioate linkages, or combinations thereof.

PCOs adopt intramolecular pseudo-cyclic structures under selected conditions (which depend upon the desired application). As used herein, "selected conditions," "desired conditions," and "conditions of interest" are used interchangeably and refer to one or more of the various conditions under which the PCOs of the invention can be used. As described more fully below, PCOs of the invention can be used as antisense oligonucleotides (in which case the "selected conditions" may be physiological) as well as for enzyme catalyzed amplifications assays (in which case the "selected conditions" are those employed for the amplification reaction, e.g., PCR). The worker of ordinary skill artisan will understand that the PCOs of the invention may need to be constructed differently to function properly under the different conditions (e.g., salt concentrations, etc.). The pseudo-cyclic structure formation has been demonstrated by thermal melting, and in vitro and in vivo nuclease stability studies presented below. Pseudo-cyclic structure formation increases resistance to degradation (nucleolytic and otherwise).

In the case where the PCO is an antisense oligonucleotide, it adopts a linear form in the presence of complementary target RNA and binds to the target RNA as indicated by thermal melting and RNase H cleavage studies. In the linear form, the functional segment hybridizes (under physiological conditions, at a minimum) to the complementary target RNA (if present) to form a duplex. This duplex is a substrate for RNase H, and, in the presence of RNase H and under the proper conditions (e.g., physiological), the RNA strand of the duplex will be cleaved by the RNase H, thereby preventing expression.

When the functional segment of the PCO according to the invention is an antisense oligonucleotide, it preferably contains at least 4 contiguous deoxyribonucleotides phosphodiesters or phosphorothioates. The sequence of at least 4 contiguous deoxyribonucleotides phosphodiesters or phosphorothioates enables a duplex formed between the functional segment and a complementary target RNA to be a substrate for RNase H for cleavage of a target RNA.

The only limitation on the nucleobases and internucleobase linkages is that they do not eliminate (a) the ability of the protective segment to hybridize to and form a duplex with the functional segment of the PCO under the desired conditions, and (b) the ability of the functional segment to carry out its intended function (e.g., in the case of a functional segment that is an antisense oligonucleotide, to hybridize to and form a duplex with a complementary RNA segment under physiological conditions, which duplex is a substrate for RNase H). Preferred nucleobases and internucleobase linkages are those that will enhance the stability of the PCO to nucleases and other forms of chemical degradation and/or enhance the ability of the functional segment to carry out its intended function. In a preferred embodiment, when the functional segment is an antisense oligonucleotide, the PCO according to the invention will comprise one or more, and preferably from two to four 2'-substituted nucleotides (preferably 2'-O substituted, more preferably 2'-O-methyl or 2'-methyoxyethyl), which are preferably at the terminal ends of the functional and/or protective segments.

In other embodiments, the functional segment can be any oligonucleobase motif that performs or induces a desired function or reaction. So, for example, the functional segment can also be a ribozyme.

Alternatively, the functional segment can have a CpG motif to induce immune stimulation, as described in U.S. Pat. No. 5,856,462.

In another embodiment, the functional segment can be a molecule-binding oligonucleobase, such as an aptamer. (Ellington and Szostak (1990) *Nature,* 346, 818–822); Famulok and Szostak (1992) *J. Am. Chem. Soc.* 114, 3990–3991; Ellington and Szostak (1992) *Nature* 355, 850–852; Tuerk and Gold (1990) *Science* 249, 505–510; Famulok and Szostak (1992) *Angew. Chem. Intl. Ed. Engl.* 31, 979–988; Bock et al. (1992) *Nature* 355, 564–566); Famulok and Szostak (1992) *Angew. Chem. Intl. Ed. Engl.* 31, 979–988; Gannon et al. (1990) *EMBO J.* 9, 1595–1602; Steven and Lane (1992) *J. Mol. Biol.* 255, 577–583). Proteins are known to interact with specific nucleotide motifs, both single stranded and double stranded nucleic acids and oligonucleotides.

Or, simply, the functional segment can be a probe for a target nucleic acid and have a nucleobase sequence that is complementary to the target.

The linker segment can be a direct bond, a mono- or oligonucleobase of 2–5 nucleobases, or other chemical moiety. The only limitation on the linker segment is that it does not eliminate the essential functions of the PCO, namely (a) the ability of the PCO to form an intramolecular pseudo-cyclic structure under the conditions of interest (e.g., physiological conditions) and (b) the ability of the functional segment to carry out its intended function. Preferred "other chemical moiety" linkers include, but are not limited to, ethylene glycol, tri(ethylene glycol), tetra(ethylene glycol), penta(ethylene glycol), hexa(ethylene glycol) and —NH$(CH_2)_n$NH—, wherein n is 2, 3, 4, 5, or 6. Alternatively, the linker segment can be a combination of the foregoing. In a preferred embodiment, the linker is a direct bond, in which case the functional and protective segments are directly bound in a 3'-3' or 5'-5' configuration.

The functional segment and the protective segment independently can be linked to the linker segment through the terminal linker end nucleobase at the nucleobase or the internucleobase linkage (which, for a nucleotide, can be the sugar or phosphate moiety). If the linker segment is a mono- or oligonucleobase, it can be linked to the functional and protective segments at its base or internucleobase linkage (e.g., sugar or phosphate moiety) as well.

In a preferred embodiment, the functional segment of the PCO of the invention is an antisense oligonucleotide for cleaving a target RNA, and a) the functional segment consists essentially of an oligonucleotide of from 11 to 50 nucleotides in length having a sequence complementary to an RNA to be cleaved, wherein the 11 to 50 nucleotides contains a sequence of from 4 to 50 deoxyribonucleotide phosphodiesters or phosphorothioates;

b) the protective segment consists essentially of an oligonucleotide of from 5 to 8 nucleotides in length and is complementary to a sequence of nucleotides within the functional segment;

c) the selected conditions are physiological conditions under which and in the absence of RNA, the protective segment and the functional segment form a duplex; and d) under physiological conditions and in the presence of RNA having a sequence of nucleotides complementary to the functional segment, the functional segment forms a duplex with the complementary RNA.

In another embodiment, the duplex formed between the functional segment and the protective segment itself can be a functional unit. For instance, the duplex can be a target for binding of an endogenous nucleic acid by triplex formation. Alternatively, the duplex can be the substrate for a duplex-binding molecule, e.g., a transcriptional factor.

In another aspect of the invention, the PCOs of the invention further comprise a "Donor" molecule and an "Acceptor" molecule. One or both of the Donor and Acceptor are capable of affecting an observable property of the other through radiative or non-radiative energy transfer when brought into close proximity. The Donor and Acceptor are attached to the PCO in a manner such that when the PCO is in a cyclic form, an observable property of the Donor and/or Acceptor changes relative to when the PCO is not in cyclic form.

As an illustrative example, in a preferred embodiment the Donor is a fluorescence energy donor ("FRED") (e.g., a fluorophore) and the Acceptor is a fluorescence energy acceptor ("FREA") (e.g., a quencher). The FRED and FREA are attached such that when the oligonucleobase is in the cyclic form (e.g., in the absence of the target nucleic acid), the FRED and FREA are brought close enough together to permit the FRED and FREA to undergo fluorescence resonance energy transfer (FRET). The result is that a change in fluorescence is observed (e.g., a change in intensity (either increase or decrease) or a change in color). For example, when the FRED is a fluorophore and the FREA a quencher, a decrease in fluorescence is observed when the two are brought in close proximity. When the functional segment binds to the complementary sequence on a target nucleic acid, the cyclic structure of the cyclicon is opened up and the fluorophore and quencher are separated far enough to disrupting FRET between the donor and acceptor molecules, resulting in spontaneous fluorescence.

Figure 8:
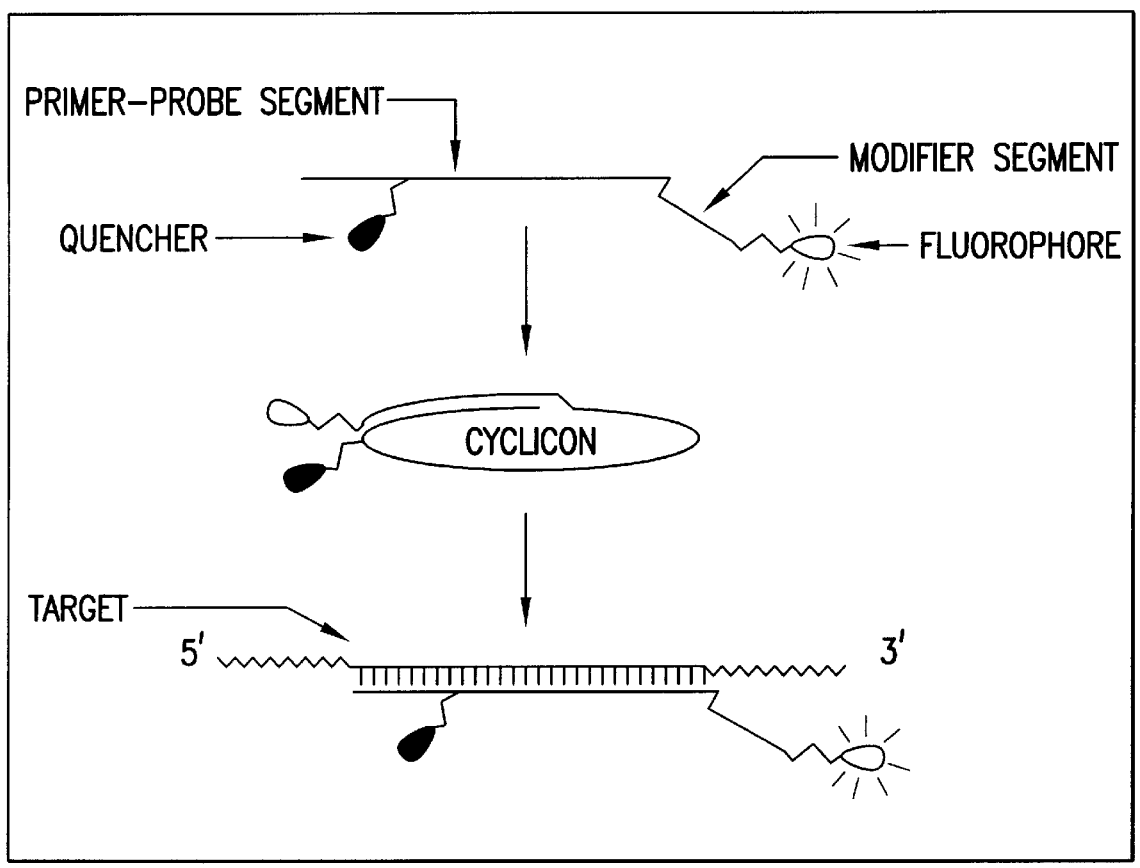
FIG. 8 displays a schematic representation of cyclicon structure and its hybridization with a complementary target nucleic acid strand. Cyclic structure formation brings fluorophore and quencher molecules in close proximity resulting in FRET. Upon binding of the cyclicon to the target strand, the cyclic structure is destabilized to open resulting in fluorescence emission.

In this embodiment, fluorescence resonance energy donor (FRED) (e.g., a fluorophore like fluorescein) is attached to the modifier oligonucleotide (i.e., protective segment), preferably at the free end (3'- or 5'-). The modifier is preferably 4 to 8 nucleobases long and is complementary to the 3'- or 5' end of the primer-probe (i.e., functional segment), which itself is preferably 15–20 nucleobases long and is complementary to a target nucleic acid. A FREA (e.g., a fluorescence quencher like DABCYL) is incorporated into the primer-probe sequence (FIG. 8). Alternatively, the FRED (e.g., a fluorophore) can be on the primer-probe sequence and the FREA can be on the modifier oligo. In yet another embodiment, both the FREA and FRED can be on the same segment such that when the functional segment of the cyclicon interacts with a target molecule with a consequent change in tertiary structure of the cyclicon, the FREA and FRED are brought in close proximity or separated such that efficient energy transfer between the two is facilitated or prevented, respectively. In general, Donor/Acceptor pairs (be they FRED/FREA or others) can be located anywhere and attached in any manner that is consistent with the ability of the PCO to form an intramolecular duplex under selected conditions, the ability of the functional segment to function for its intended purposes, and the ability of detectable energy transfer (e.g., fluorescence) to occur upon opening of the PCO from its cyclic state.

In the absence of the target nucleic acid, cyclicons form intramolecular cyclic structures; in this state, the fluorophore and the quencher are brought in close proximity to each other (FIG. 8), resulting in the loss of fluorescence because of FRET. In the presence of a target nucleic acid sequence in solution, the probe sequence hybridizes to the complementary sequence on the target, destabilizing the intramolecular cyclic structure and causing it to open up, resulting in spontaneous fluorescence emission. The presence of fluorescence indicates hybridization between the target nucleic acid and the probe sequence of the cyclicon (FIG. 8).

Generally, cyclicons with 5'-5' linked primer-probe/modifier oligo have lower background fluorescence than 3'-3' attached cyclicons. This difference could reflect the greater distance between the fluorophore and quencher in 3'-3' attached cyclicons as a result of 3'-skewing of the two strands of the duplex DNA. It is appropriate not to skip a base between the fluorophore and quencher in 3'-3' attached cyclicons to reduce background fluorescence. The optimum distance between the FRED and FREA molecules is about 70 to 100 Å to disrupt FRET and attain full fluorescence (49,50). Preferably a distance of about nineteen internucleotide phosphate bridges between the donor and acceptor molecules is maintained. In such a configuration, when the cyclicon hybridizes to the target nucleic acid sequence, the FRED and FREA molecules are pulled apart about 70 Å, effectively diminishing FRET between the molecules and resulting in spontaneous fluorescence emission. It is a routine matter for one of ordinary skill in the art to determine suitable placement of donor and acceptor molecules on the oligonucleobase such that energy transfer between the two is possible when the cyclicon is in the circular state but not possible in the linear state, or visa versa.

The protective and functional segments are linked via the linker segment in either a 3'-3' or 5'-5' configuration as required for the application of the cyclicon. For example, for use in cellular studies, a 3'-3' linkage would be more appropriate because of the higher stability of 3'-3'-attached oligonucleotides against nucleases in in vitro and in vivo studies (6), whereas for a primer in PCR reactions, a free 3'-end containing 5'-5'-attached cyclicon is more appropriate.

Cyclicons bearing Donor/Acceptor pairs (e.g., a FRED/FREA pair) can be used to measure the concentration of specific mRNAs or cDNAs in whole cellular extracts or enzyme-amplified (e.g., PCR) nucleic acids (e.g., DNA), in homogeneous environment (liquid phase) or where the probe is attached to a solid phase. Cyclicons according to this aspect of the invention are also useful as primers or integrated primer-probes in enzyme catalyzed amplification reactions (e.g., real-time PCR) for monitoring nucleic acid amplification. For uses as a primer or primer-probe in enzyme catalyzed amplification, the functional segment is complementary to the terminal portion of the nucleic acid to be amplified. When used as a primer or primer-probe in an enzyme catalyzed amplification, the cyclicon itself can be linked to the solid surface or it can be a component with the solution being contacted with the solid surface. See FIGS. 20 and 21.

Cyclicons according to the invention offer advantages over the TAQMAN® probe in which a probe is labeled with a quencher and fluorophore on either end. The TAQMAN® probe is cleaved by the 5'-exonuclease activity of DNA polymerase during PCR, releasing free fluorophore and thereby increasing the fluorescence signal. The probe function of the cyclicons is independent of nuclease activity of the polymerase, and, therefore, can be used with polymerases devoid of nuclease activity. Nucleases devoid of polymerase activity are much cheaper than polymerases that come with nuclease activity subunit. The integrated primer-probe function of cyclicons is an important step forward in PCR detection and diagnostics without compromising the total length of the oligonucleotide (compared with the length and modifications incorporated in the scorpion) and costs. In addition, the use of a unified primer-probe in PCR detection simplifies the reaction set-up and avoids unnecessary carry-over contaminations.

A number of donor/acceptor molecules suitable for use as FREDs and FREAs are known in the art. Those skilled in the art are referred to U.S. Pat. No. 5,866,336 (the '336 patent) for its teachings regarding such molecules. Such molecules can be linked to the cyclicons of the invention on the base moiety of the nucleobase or a oligonucleobase backbone moiety (e.g., the 2' position of a nucleotide sugar residue). For example, Yamana et al., *Nucleic Acids Res.* 27, 2387 (1999) teaches 2'-pyrene modified oligonucleotides as highly sensitive probes of RNA. Also, Barrio et al., *Biochem. Biophys Res. Commun.* 46, 597 (1972) teach the fluorescent adenosine and cytidine derivatives.

Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), Cy3, Cy5, and 5-(2'-aminoethyl) aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

FRET labels have been incorporated into immunofluorescent assays used to detect specific antigens (Ullman et al. U.S. Pat. Nos. 2,998,943; 3,996,345; 4,160,016; 4,174,384; and 4,199,559). Several patents teach the application of energy transfer for polynucleotide hybridization (U.S. Pat. Nos. 4,996,143, 5,532,129, and 5,565,322).

European Patent Application publication number EP 0 229 943 A2 teaches specified distances between donor and acceptor for maximum FRET. It also discloses that the donor and acceptor labels can be located on the same probe.

A similar application of energy transfer was disclosed by Cardullo et al. in a method of detecting nucleic acid hybridization (1988, Proc. Natl. Acad. Sci. USA, 85: 8790–8794 and WO 92/14845). Fluorescein (donor) and rhodamine (acceptor) are attached to 5' ends of complementary oligodeoxynucleotides.

Other publications have disclosed the use of energy transfer in a method for the estimation of distances between specific sites in DNA (Ozaki and McLaughlin, 1992, Nucl. Acids Res., 20: 5205–5214), in a method for the analysis of structure of four way DNA junction (Clegg et al. 1992, Biochem., 31: 4846–4856), and in a method for observing the helical geometry of DNA (Clegg et al., 1993, Proc. Natl. Acad. Sci. USA, 90: 2994–2998).

The '366 patent discloses the use of FRED/FREA pairs in synthetic analogs of naturally occurring hairpin structures.

The cyclicons of the present invention are structurally distinct, non-naturally occurring constructs comprising at least two terminal sequences (the functional segment and the protective segment) of opposite polarity, resulting in a molecule having two 3' or two 5' ends. This feature results in different physicochemical characteristics; they also generally permit cyclicons to consists of fewer nucleobases and, therefore, are less expensive to prepare.

As should be clear from the foregoing, all or any portion of the functional segment can give the PCO its functionality. Thus, for example, where the functionality of the PCO is as an antisense agent, the entire functional segment or only a portion of it can be antisense to the target. Or, as another example, where the functionality of the PCO is for binding of a protein to the PCO duplex (palindromic or decoy), the functionality resides in the sequence of nucleotides within the functional segment that is complementary to the protective segment, i.e., the sequence that participates in duplex formation.

PCOs according to the invention may be conveniently synthesized on a suitable solid support using well known chemical approaches, including, for oligonucleotides, H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon (1993) Methods in Molec. Biol. 20, 465).

PCOs according to the invention can be used for any purpose that its constituent functional segment oligonucleobase can be used. For example, they can be used as "probes." They can also be used to elucidate the biological and/or physiological function of a targeted gene by being used to inhibit the activity of the gene in an experimental cell culture or animal system. In such applications, the PCOs of the invention are used to effect cleavage of a target mRNA molecule by contacting the PCO with the target mRNA in the presence of an RNase H, which cleaves the RNA of RNA/DNA duplexes. This is accomplished in vitro or in vivo by administering to a cell or an animal, respectively, a PCO according to the invention wherein the functional segment comprises an antisense oligonucleobase (preferably oligonucleotide) complementary to the target mRNA and observing the effects. In this use, PCOs according to the invention are preferable to traditional "gene knockout" approaches because they are easier to use and can be used to inhibit gene activity at selected stages of tumor development or differentiation.

When the functional segment is an antisense oligonucleobase (preferably oligonucleotide), PCOs according to the invention are also useful in therapeutic approaches in which inhibition of gene expression is desired. This can include, for example, inhibition of an endogenous gene (e.g., an oncogene) or an exogenous gene (e.g., a gene essential for growth and/or metabolism of a pathogen).

PCOs according to the invention can be used in solution phase or in the solid phase, e.g., attached to a biochip or magnetic beads for high-throughput nucleic acid screening and solid phase PCR. The attachment can be at either end of the PCO (i.e., the protective segment terminus or the functional segment terminus), or anywhere within the functional, protective, or linker segments, and can be by any convenient means known in the art. PCOs can be used in DNA or oligonucleotide microarrays on solid supports (glass, membrane, fiber optics, silicon chips, etc) for gene expression profiling and analysis, diagnostics, toxicology, detection of genetic mutations, single nucleotide polymorphism analysis, molecular pharmacology, etc. E.g., Case-Green et al., *Current Opnion in Chem Biol.* 2, 404 (1998). The use of PCOs according to the invention in solid phase detection, for example, offers a number of advantages over conventional detection-on-a-chip techniques, as displayed in FIG. 19. Whereas the quality control of each fluorescent spot is difficult and qualitative in convention chip technology, the use of PCOs of the invention permits precise quantization. Convention detection on a chip requires a separate probe with a detection tag, resulting in a two step detection process: 1) initial hybridization with the target nucleic acid, and 2) a secondary hybridization between the target nucleic acid and the detection probe. By contrast, PCOs permit hybridization and detection in a single step.

Figure 20:
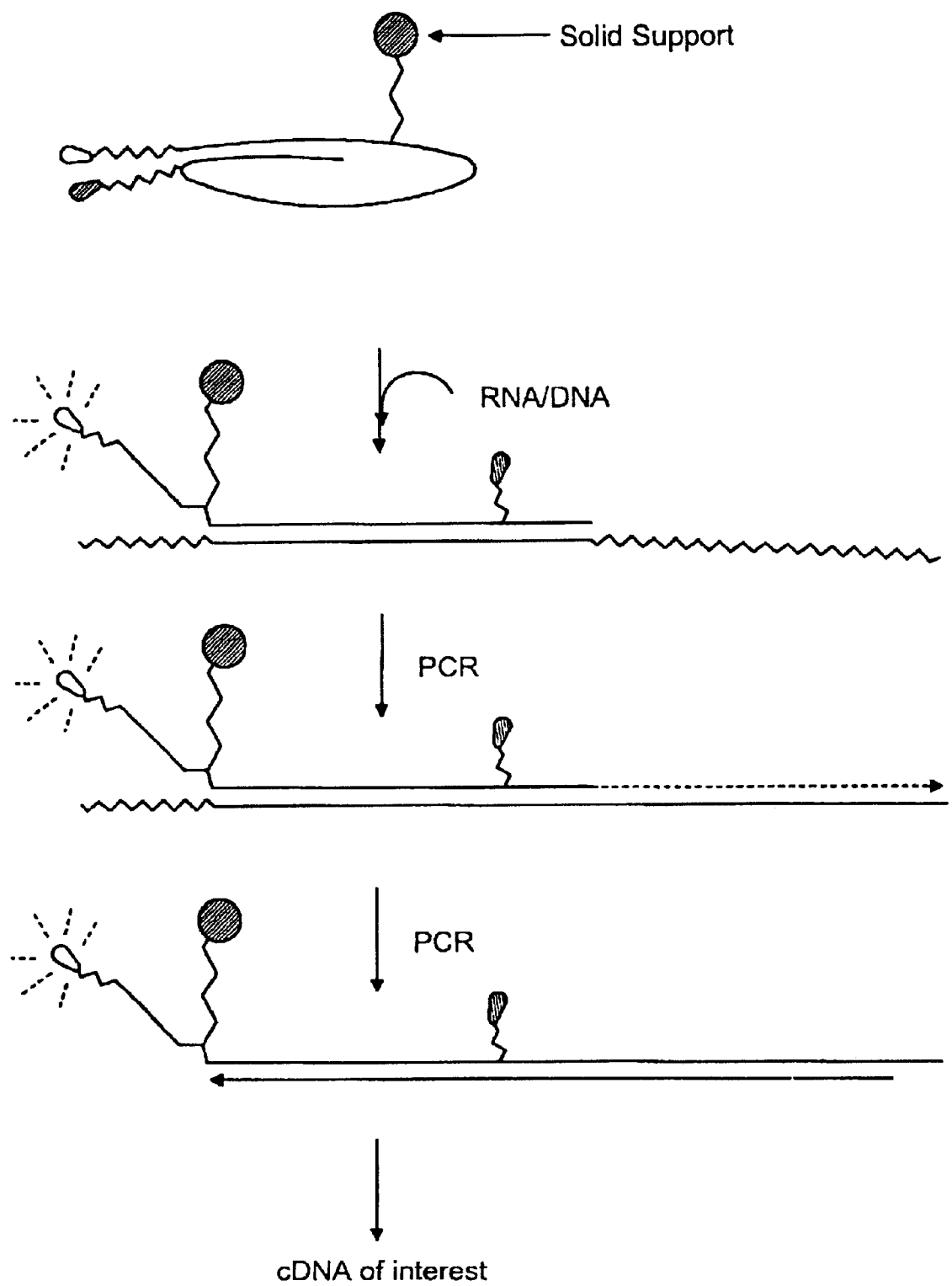
FIG. 20 presents a schematic representation of PCR using a PCO attached to a solid support according to the invention.

FIG. 20 displays a schematic diagram in which a PCO labeled with Donor/Acceptor pair is linked to a solid surface, wherein the functional segment of the PCO is complementary to a target nucleic acid to be amplified by PCR (although other enzymatic amplification protocols could be employed). During amplification, when the PCO is involved in intermolecular hybridization, a detectable signal is emitted by the Donor molecule (e.g., FRED).

Figure 21:
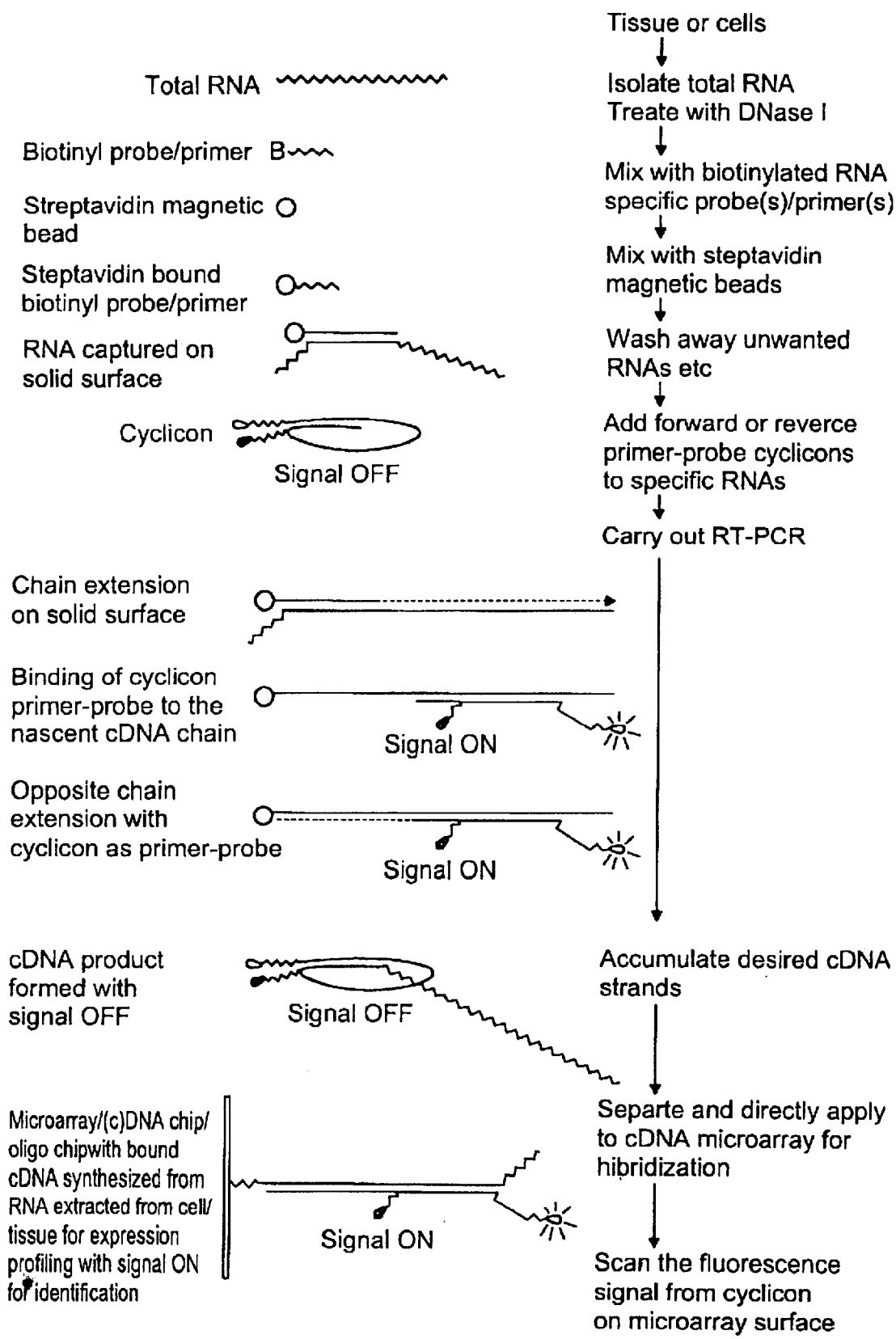
FIG. 21 presents a schematic representation in which a PCO of the invention is used in solution phase amplification of a target nucleic acid, enabling one step amplification and labeling of the target nucleic acid with subsequent detection on a chip.

FIG. 21 displays a schematic diagram in which the functional segment of a PCO labeled with Donor/Acceptor pair serves as a primer-probe. Amplification results in a labeled nucleic acid that can be applied directly to a microarray cDNA chip. This method avoids the necessity to purify, isolate and label the cDNA before hybridization to a cDNA gene microarray. In addition there is no need to conduct separate reactions for identification of different RNAs (or gene expressions). Different biotinylated primers/probes and different cyclicons for each specific RNA can be employed for amplification and the resulting solution directly applied to a microarray, without further separation, isolation, or labeling to identify which genes are expressed. Because first recognition of RNA comes from biotinylated primer/probe and the second recognition comes from cyclicon primer-probe, specificity of amplification should be much higher than regular amplification procedures, thereby reducing false positives.

Another aspect of the invention comprises PCOs adapted for linkage to a solid surface. Such PCOs comprise PCOs according to the invention that have a chemical moiety attached thereto that facilitates the linkage of the PCO to the solid support (e.g., glass, silicon chips, magnetic beads, membranes (e.g., nylon membranes), 96-well plastic plates, etc.) Such chemical moieties include those for covalent linkage to a solid support, such as $C_1$–$C_{12}$alkylamino linkers optionally substituted with hydroxy-$C_1$–$C_6$alkyl, $C_1$–$C_{12}$alkylsuccinimides, thiol, as well as those for non-covalent linkage, such as biotin, avidin, or streptavidin (for binding to a solid support bearing its conjugate pair). Such chemical moieties can be attached anywhere within the PCO (so long as it does not interfere with the basic function of the functional segment or prevent intramolecular duplex formation) using conventional techniques. In embodiments in which functional segment is constructed to hybridize to a complementary target molecule (e.g. an mRNA), a segment of at least 6 nucleobases on the terminal end of the functional segment will be complementary to the target and single-stranded when the PCO forms an intramolecular duplex. In such embodiments, the PCOs hybridize to the target sequence in two steps. The first step involves hybridization of the single stranded region of the PCO to the target sequence. The stability of the intermolecular duplex thereby formed then forces the intramolecular duplex of the PCO to destabilize and allows complete hybridization to the target. Since there are two steps in recognition, such PCOs are more specific in detecting complementary RNA than their linear counterparts. The use of PCOs as probes in solution or on solid phase (either by the 3' or 5' termini or through the bases) will be more specific than their linear counterparts.

Studies presented below show that PCOs containing antisense functional segments maintain antisense activity in cell cultures. The advantage foreseen with these PCOs is that their formation of intramolecular pseudo-cyclic structures allows for less interaction with non-targeted macromolecules (including nucleic acids and proteins) and, also reduced polyanionic-related side effects, and will linearize in the presence of the target mRNA only.

In another aspect, the invention is a kit. In this aspect, the kit will comprise at least one PCO of the invention and one or more other reagents that facilitate use of the PCO. In specific embodiments, the kits comprise one or more PCOs for use in enzyme catalyzed nucleic acid amplification (e.g., PCR, RT-PCR) in one or more containers and further comprises additional components for carrying out the amplification reactions. Where the target nucleic acid sequence being amplified is one implicated in disease or disorder, the kits can be used for diagnosis or prognosis. In a specific embodiment, a kit is provided that comprises, in one or more containers, PCOs for use as forward and reverse primers for carrying out amplification, and optionally, a DNA polymerase or other polymerase (e.g. a reverse polymerase for use in RT-PCR) with and without exonuclease activity. A kit for triamplification can further comprise, in one or more containers, a blocking oligonucleotide, and optionally DNA ligase.

PCOs in containers can be in any form, e.g., lyophilized, or in solution (e.g., a distilled water or buffered solution), etc. PCOs and other reagents ready for use in the same amplification reaction can be combined in a single container or can be in separate containers.

In another embodiment of this aspect of the invention, a kit for the detection of a selected target DNA target sequence comprises in one or more containers (a) primers for enzyme catalyzed amplification, one or both of which are PCOs labeled with fluorescent and quenching moieties; and optionally: (b) a control DNA target sequence; (c) an optimized buffer for amplification; (d) appropriate enzymes for the method of amplification contemplated, e.g., a DNA polymerase for PCR or triamplification or SDA, a reverse transcriptase for NASBA; (d) a set of directions for carrying out amplification, e.g., describing the optimal conditions, e.g., temperature, number of cycles for amplification. Optionally, the kit provides (e) means for stimulating and detecting fluorescent light emissions, e.g., a fluorescence plate reader or a combination thermocycler-plate-reader to perform the analysis.

The following examples are provided for illustrative purposes only and are not intended, nor should they be construed as limiting the invention in any manner. Those skilled in the art will appreciate that variations and modifications can be made without deviating from the spirit and scope of the present invention.

EXAMPLES

Example 1

Synthesis and Analysis of Oligonucleotides

To study the therapeutic potential of PCOs, we have used a PS-oligonucleotide (18-mer) complementary to the regulatory subunit of PKA (RIα) (7,32). An antisense oligonucleotide complementary to this region of PKA RIα mRNA has been studied in detail in vitro and in vivo models (7,32,33) and is currently being evaluated in human clinical trials.

The synthesis of oligonucleotides was carried out on a 1-μmole scale on a Biosearch 8900 DNA synthesizer using deoxynucleoside-3'-phosphoramidites (Perseptive Biosystems, Framingham, Mass.) for chain elongation from the 3'- to 5'-end and deoxynucleoside-5'-phosphoramidites (Glen Research, Sterling, Va.) for chain elongation from the 5'- to 3'-end. All oligonucleotides, except oligonucleotide SEQ. ID NO.:1, were synthesized in two steps. First, oligonucleotides (except oligonucleotides SEQ. ID NOs.:2 and 3) were synthesized from the 5'- to the 3'-end by using 3'-dimethoxytrityl-deoxynucleoside-CPG (Glen Research, Sterling, Va.) and appropriate deoxynucleoside-5'-phosphoramidites using a modified RNA synthesis program in which the detritylation time and detritylation solution volume were doubled compared to the standard RNA synthesis program. The second part of the oligonucleotides (except for oligonucleotides SEQ. ID NOs.:2 and 3) was synthesized from the 3'- to the 5'-end by using deoxynucleoside-3'-phosphoramidites and a standard DNA synthesis program. Oligonucleotides SEQ. ID NOs.:2 and 3 were synthesized first from the 3'- to the 5'-end, then from the 5'- to the 3'-end using appropriate CPG support bound nucleoside, nucleoside phosphoramidites, and a synthesis program. Oligonucleotide SEQ. ID NO.:1 was synthesized using deoxynucleoside-3'-phosphoramidites and a standard DNA synthesis program. Oxidation following each coupling was carried out using 3H-1,2-benzodithiol-3-one-1,1-dioxide to obtain a phosphorothioate linkage or using iodine reagent to obtain a phosphodiester linkage as desired. Deprotection of all oligonucleotides was completed by incubating with the concentrated ammonium hydroxide solution at 65° C. overnight. Oligonucleotides were purified using preparative polyacrylamide gel electrophoresis and desalted using C18 Sep-Pak cartridges (Waters). Analysis of the oligonucleotides was carried out using capillary gel electrophoresis (CGE). The purity of the oligonucleotides based on A260/mass ratio was >98%, and based on CGE was 95%, rest being n-1, n-2, etc., products.

For the present studies, we selected an 18-mer PS-oligonucleotide (SEQ. ID NO.:1) that is complementary to the mRNA of regulatory subunit of protein kinase A (RIα) and has been shown to be effective in inhibiting the growth of various cancer cells in vitro and the growth of tumors in mouse xenograft models by a sequence-specific antisense mechanism (7,32,33).

PCOs containing phosphodiester functional segment: First, we synthesized oligonucleotide SEQ. ID NO.:2, (FIG. 7) which has an 18-mer phosphodiester oligonucleotide (PO-oligonucleotide) as the functional segment and a 6-mer as the protective PO-oligonucleotide linked by their 5'-5'-ends. As a control, we synthesized oligonucleotide SEQ. ID NO.:3 (FIG. 7) in which the functional segment is the same as in oligonucleotide SEQ. ID NO.:2, but which contains two mismatches in the protective PO-oligonucleotide.

Example 2

Synthesis of $^{35}$S-labeled Oligonucleotide

For $^{35}$S-labeling, oligonucleotide SEQ. ID NO.:8, which contained four H-phosphonate linkages at the 5'-end of functional segment, was synthesized. For labeled product, synthesis of oligonucleotide SEQ. ID NO.:8 was carried out in three steps—the first and second steps were carried out as described above. In the third step, the last four couplings were carried out using nucleoside-H-phosphonate and H-phosphonate chemistry. Oxidation of the last four H-phosphonate linkages was carried out with $^{35}$S-elemental sulfur (0.5–2.5 Ci/mg, Amersham) as reported earlier (34). $^{35}$S-labeled oligonucleotide SEQ. ID NO.:8 was purified using preparative 20% polyacrylamide gel electrophoresis and desalted using C18 Sep-Pak cartridges. The specific activity of oligonucleotide SEQ. ID NO.:8 obtained was 0.2 μCi/μg.

Example 3

Thermal Melting Experiments

Melting temperatures of oligonucleotides alone and in the presence of complementary RNA were determined in a buffer containing 100 mM NaCl, 5 mM $MgCl_2$, 0.1 mM $Na_2EDTA$, and 10 mM sodium phosphate, pH 7.4 (23). Each oligonucleotide was taken alone or mixed with complementary RNA at a 1:1 ratio in an eppendorf tube and dried in a speed vac, and resuspended in 1 ml of buffer. The final concentration of the oligonucleotide in each sample was 1 μM and the final concentration of the complementary RNA was 1 μM. The samples containing oligonucleotide alone were heated at 85° C. for 2 min and cooled immediately on ice for 5 min to allow formation of intramolecular duplexes. The samples containing oligonucleotide with the complementary RNA were incubated at room temperature (21° C.) for 1 hr. Then the UV absorbance curves as a function of temperature were recorded on a Lambda 20 UV/Vis Spectrometer (Perkin-Elmer) at 260 nm using a linear movement multicell holder (6 cells). The temperature was controlled by a PTP-6 Peltier System attached to the Spectrometer. The heating rate was 0.5° C./min. The data were collected on a Dell computer interfaced with the instrument and processed with UV-WinLab software came with the instrument. The melting temperatures ($T_m$s) were measured from first derivative curves. Each $T_m$ value was an average of at least two measurements and the reproducibility was within ±1.0° C.

The $T_m$ of oligonucleotide SEQ. ID NO.:2 alone was 51.9° C., whereas oligonucleotide SEQ. ID NO.:3 alone showed a broad transition without a defined $T_m$, indicating that functional segment hybridizes to the complementary 6-mer protective segment and forms an intramolecular pseudo-cyclic structure as shown in FIG. 1. Alternately, oligonucleotide SEQ. ID NO.:2 can form a linear tandem intermolecular complex under experimental conditions. However, such a linear intermolecular complex would have a lower $T_m$ than that observed for oligonucleotide SEQ. ID NO.:2 alone. In addition, we did not observe any slow moving bands on non-denaturing gels ruling out the possibility of formation of linear tandem structures (data not shown). Oligonucleotide SEQ. ID NO.:3, which had two mismatches in the protective segment, fails to hybridize with the functional segment and remains in the linear form.

In the presence of the complementary RNA, oligonucleotides SEQ. ID NOs.:2 and 3 had $T_m$s of 76.7° C. and 76.8° C., respectively, suggesting that the functional segments of oligonucleotides SEQ. ID NOs.:2 and 3 hybridized to the target RNA and formed stable heteroduplexes. The $T_m$s were recorded by mixing the hybridized form of oligonucleotide SEQ. ID NO.:2 and the complementary RNA at room temperature (21° C.) rather than heated to 85° C., and then cooling the mixture to destabilize the intramolecular pseudo-cyclic structure of oligonucleotide SEQ. ID NO.:2 to favor duplex formation with the RNA. These results suggest that the intramolecular pseudo-cyclic structure of oligonucleotide SEQ. ID NO.:2 destabilizes by itself in the presence of the complementary RNA and forms a stable heteroduplex. The thermal stability of the duplex of oligonucleotide SEQ. ID NO.:2 and the RNA was higher than the thermal stability of the intramolecular pseudo-cyclic structure of oligonucleotide SEQ. ID NO.:2 (FIG. 7) which would also favor destabilization of the pseudo-cyclic structure of oligonucleotide SEQ. ID NO.:2.

Thermal melting studies showed that oligonucleotide SEQ. ID NO.:6 alone had a broad transition, whereas oligonucleotides SEQ. ID NOs.:7–9 alone had $T_m$s of 48° C., 50.2° C., and 55.3° C., respectively. These results suggest that oligonucleotide SEQ. ID NO.:5, in which the protective segment was only five nucleotides long, did not form a stable pseudo-cyclic structure with the 5'-region of the functional segment (PS-oligonucleotide). The stability of the pseudo-cyclic structures of oligonucleotides SEQ. ID NOs.:7–9, in which the length of protective segment increased from six bases to eight bases long, respectively, increased progressively. Oligonucleotides SEQ. ID NOs.:10 and 11, which contained mismatches in the protective segment, showed broad melting transitions without definitive $T_m$s. In the presence of the complementary RNA, oligonucleotides SEQ. ID NOs.:6–11 showed similar $T_m$s (FIG. 7) suggesting that all oligonucleotides adopted the linear form in the presence of RNA and formed heteroduplexes.

Example 4

Nuclease-stability of Oligonucleotides

One $A_{260}$ Unit of oligonucleotide was heated to 90° C. for 2 min in a buffer containing 100 mM NaCl, 2 mM $MgCl_2$, 25 mM Tris-HCl, pH 7.5, and then cooled down to 0° C. quickly. The annealed samples were incubated with snake venom phosphodiesterase (0.1 μg, Boehringer Mannheim) at 37° C. for 5 min or 30 min. The digestion was stopped by heating to 90° C. for 5 min. The digested oligonucleotides were desalted using C18 Sep-Pak cartridges before analysis by CGE (Model 2200, Beckman Instruments).

Figure 2:
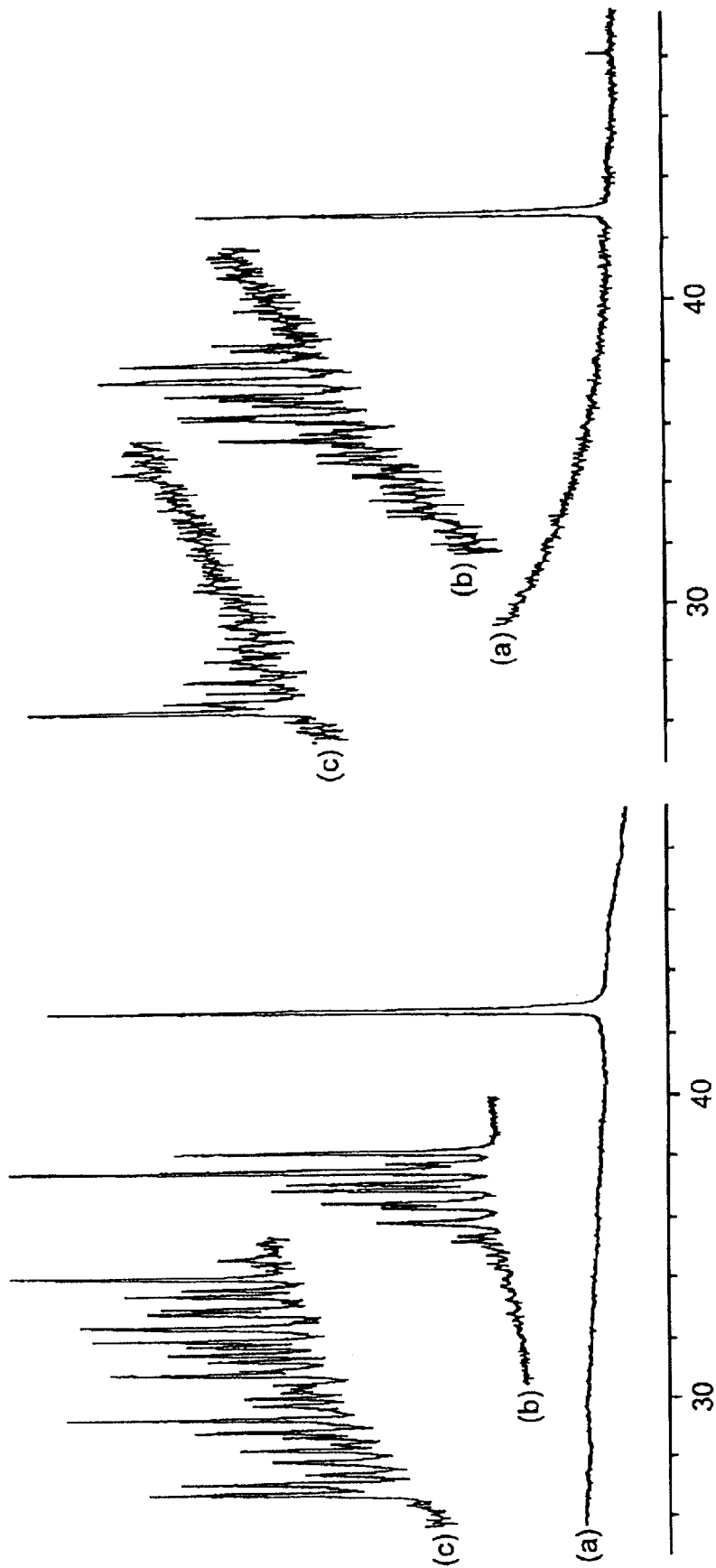
FIGS. 2A and 2B show capillary gel electrophoresis profiles of oligonucleotides SEQ. ID NO.:2 (FIG. 2A) and SEQ. ID NO.:3 (FIG. 2B) in the presence of snake venom phosphodiesterase at time points a) 0 min, b) 5 min, and c) 30 min in both the panels.

To determine if the pseudo-cyclic form of oligonucleotide SEQ. ID NO.:2 confers upon it greater nuclease stability than found with oligonucleotide SEQ. ID NO.:3, both oligonucleotides SEQ. ID NOs.:2 and 3 were incubated with snake venom phosphodiesterase (SVPD). Aliquots of the incubation mixtures were removed at 0, 5 and 30 min, and analyzed by CGE. FIG. 2 shows that oligonucleotide SEQ. ID NO.:2 was relatively more stable than oligonucleotide SEQ. ID NO.:3: intact oligonucleotide SEQ. ID NO.:2 was still detectable after 30 mins, whereas oligonucleotide SEQ. ID NO.:3 was completely degraded even at the 5-min time point under the same experimental conditions. These results suggest that in spite of the presence of two 3'-ends in these oligonucleotides, only oligonucleotide SEQ. ID NO.:2 is stable against the 3'-exonuclease SVPD because of the presence of the intramolecular pseudo-cyclic structure.

In the next step we synthesized and studied oligonucleotides SEQ. ID NOs.:4 and 5 in which antisense and protective PO-oligonucleotides were linked by 3'-3'-linkages. Oligonucleotides SEQ. ID NOs.:4 and 5 had $T_m$s similar to those of oligonucleotides SEQ. ID NOs.:2 and 3, respectively (FIG. 7). In nuclease stability experiments against spleen phosphodiesterase (a 5'-exonuclease), oligonucleotide SEQ. ID NO.:4, which exists in a pseudo-cyclic form, was stable (as in the case of oligonucleotide SEQ. ID NO.:2); oligonucleotide SEQ. ID NO.:5, which cannot form a intramolecular pseudo-cyclic structure, was digested completely (as in the case with oligonucleotide SEQ. ID NO.:3; data not shown). These results suggest that pseudo-cyclic structure formation provides antisense oligonucleotides with stability against exonucleases.

Encouraged by these results, we synthesized oligonucleotides SEQ. ID NOs.:6–9, which consisted of 18-mer PS-oligonucleotide as the functional segment and PO-oligonucleotide as the protective segment linked through their 3'-ends (3'-3'-linkage). The length of the protective segment varied from 5- to 8-mer (oligonucleotides SEQ. ID NOs.:6–9, respectively) (FIG. 7). As controls, we synthesized oligonucleotides SEQ. ID NOs.:10 and 11 containing two and three mismatches, respectively, in the protective segment. These controls corresponded to oligonucleotides SEQ. ID NOs.:6 and 9 in length. Oligonucleotide SEQ. ID NO.:1, an 18-mer PS-oligonucleotide without a protective segment appendage, was synthesized for comparison.

Example 5

RNase H Mediated Cleavage Experiments

RNA was labeled with $^{32}P$ at the 5'-end using T4 polynucleotide kinase (Pharmacia) and [γ-$^{32}P$]ATP (Amersham), as reported earlier (24). Oligonucleotides SEQ. ID NOs.:1, 6, 8, 10, and 11 were dissolved in 10 μl buffer (30 mM HEPES.KOH, pH 8.0, 75 mM KCl, 6 mM $MgCl_2$, 1.5 mM DTT, 75 μg/ml BSA), heated at 85° C. for 1 min., and then cooled on ice for 5 min. About 50,000 CPM of $^{32}P$-end labeled RNA in 4 μl of water was added to the annealed oligonucleotide in buffer solution (10 μl), and incubated at 37° C. for 10 min. RNase H (0.65 μl of 1:10 diluted; Pharmacia) was added to the mixture, and incubated at 37° C. for 10 min. The reaction was stopped by the addition of 1 μl of 0.5 M EDTA and 20 μl of formamide, and analyzed using 20% denaturing polyacrylamide gel electrophoresis and autoradiography.

Figure 3:
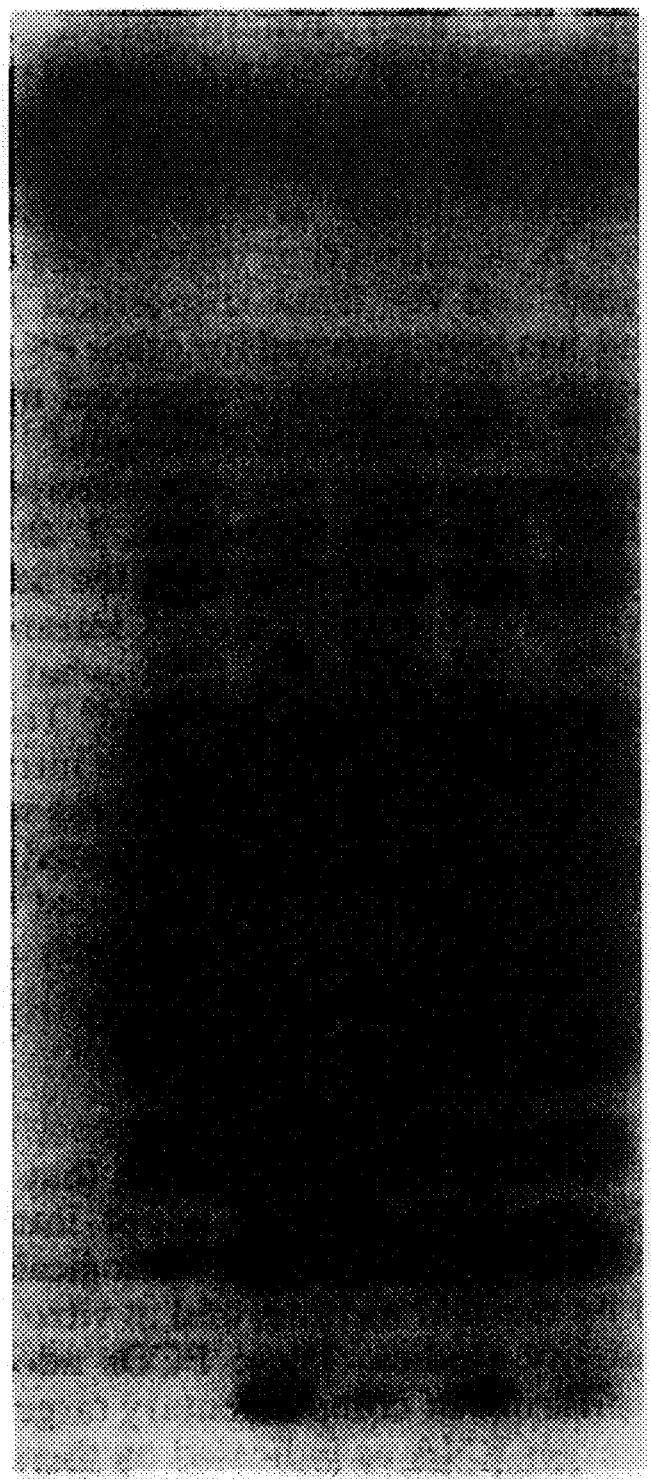
FIG. 3 shows the RNase H cleavage profile of $5'$-$^{32}$P-labeled RNA in the presence of oligonucleotides SEQ. ID NOs.:1, 6, 8, 10 and 11 in lanes 2–6, respectively. Lane 1, labeled C, represents control in the absence of antisense oligonucleotide.

Oligonucleotides SEQ. ID NOs.:5–11 were incubated with the complementary RNA that was labeled at the 5'-end with $^{32}P$ and RNase H. RNase H binds to the DNA-RNA heteroduplex and cleaves RNA at the 3'-end of the RNA of the heteroduplex (24). The cleavage pattern of RNA in the presence of oligonucleotides SEQ. ID NOs.:6–11 was similar to that of oligonucleotide SEQ. ID NO.:1 (FIG. 3), suggesting that these oligonucleotides adopted a linear form in the presence of the complementary RNA and that all oligonucleotides formed heteroduplexes with the target RNA; these heteroduplexes were substrates for RNase H, which is one of the important properties required for antisense activity.

Example 6

In vivo Stability of Oligonucleotides

Oligonucleotides SEQ. ID NOs.:1, 6, and 8 were administered intravenously to CD-1 mice (20–25 gms) at a dose of 50 mg/kg. Blood was collected from mice at 1 and 3 hr after administration in heparinized tubes. The plasma (100 ml) was incubated with proteinase K (60 μg, Sigma) in extraction buffer (0.5% SDS, 10 mM NaCl, 20 mM Tris-HCl, pH 7.6, 10 mM EDTA) for 2 hr at 60° C. The samples were extracted twice with phenol/chloroform (1:1, v/v) and precipitated with ethanol after addition of glycogen (1 μg). The samples were 5'-end labeled with [γ-$^{32}P$]ATP (Amersham)

using T4 polynucleotide kinase (10 Units, New England Biolabs), and then analyzed using 20% denaturing polyacrylamide gel electrophoresis and autoradiography.

Figure 5:
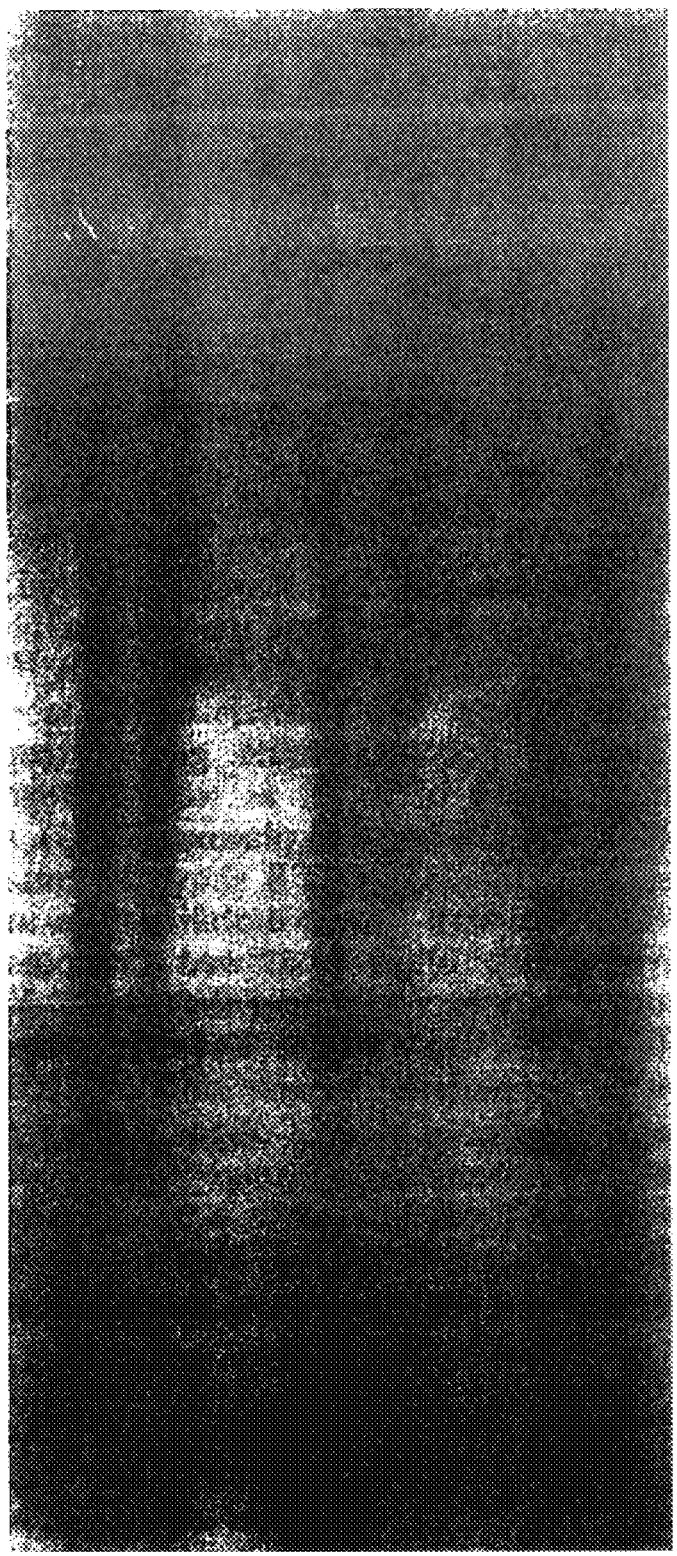
FIG. 5 shows the in vivo stability of oligonucleotides SEQ. ID NOs.:1, 6, and 8 in plasma at 1 hr (lane 2) and 3 hr (lane 3) after administration to mice.

Having established that oligonucleotides SEQ. ID NOs.:6–9 adopt intramolecular pseudo-cyclic forms under physiological conditions, adopt a linear form in the presence of the complementary RNA, maintain binding affinity to activate RNase H, and have biological activity, we were interested in examining the in vivo nuclease stability of these oligonucleotides compared to oligonucleotide SEQ. ID NO.:1. We studied three oligonucleotides, SEQ. ID NOs.:1, 6, and 8, for their comparative in vivo stability. We administered these three oligonucleotides intravenously to mice at a dose of 50 mg/kg. At 1 and 3 hr after administration, blood was collected in heparinized tubes and plasma samples were prepared. Oligonucleotides were extracted from the plasma using the protocols reported earlier (35) and labeled with $^{32}$P using polynucleotide kinase. The analysis of the labeled oligonucleotides by polyacrylamide gel electrophoresis showed the presence of intact as well as degradation products of oligonucleotides SEQ. ID NOs.:1, 6, and 8, in plasma (FIG. 5).

Analysis of the results of oligonucleotides SEQ. ID NOs.: 6 and 8 showed primarily the presence of bands with slower mobility than intact 18-mer oligonucleotide SEQ. ID NO.:1, while oligonucleotide SEQ. ID NO.:1 showed the presence of degradation products, suggesting that the 3'-3'-linkage between the protective segment and the functional segment provides increased nuclease stability. Comparison of the degradation products of oligonucleotides SEQ. ID NOs.:6 and 8, which have a 5- and a 7-mer protective segment, respectively, suggest that oligonucleotide SEQ. ID NO.:7 is more stable than oligonucleotide SEQ. ID NO.:5. Oligonucleotide SEQ. ID NO.:7 forms a more stable intramolecular pseudo-cyclic structure than oligonucleotide SEQ. ID NO.:5 (vide infra $T_m$ data). It is worth mentioning that degradation of oligonucleotides SEQ. ID NO.:6 and SEQ. ID NO.:8 produces an 18-mer PS-oligonucleotide (oligonucleotide SEQ. ID NO.:1) that contains at least one nucleotide attached via a 3'-3'-linkage as the intermediate product, which provides increased stability (see FIG. 5).

Example 7

Pharmacokinetics and Tissue Disposition

Oligonucleotide SEQ. ID NO.:8 was administered subcutaneously at a dose of 2 mg/kg (a mixture of unlabeled and $^{35}$S-labeled oligonucleotide SEQ. ID NO.:8) in 100 μl saline to CD-1 male mice (20–24 gm; Charles River, Wilmington, Mass.). At 3, 48 and 96 hr after administration, two mice at each time point were euthanized by exposure to metofane (Malinkrodt Veterinary, Mundelein) followed by cervical dislocation. Blood was collected in EDTA containing tubes (Becton Dickinson, Franklin Lakes, N.J.). Liver, kidney, spleen, heart and lungs were removed and blotted on a piece of gauze, weighed and stored at −20° C. For counting of $^{35}$S, 50 μl of plasma was added to 1 ml TS-2 (Research Product International, Mt. Prospect, Ill.), swirled, and mixed with 250 μl 10% glacial acetic acid. The sample was swirled again until uniform, then 18 ml of 3a70B scintillation cocktail (Research Product International) was added. Samples were prepared in triplicate and incubated overnight at room temperature before counting. Pieces of tissues in triplicate weighing between 10–50 mg were placed in scintillation vials to which was added 1 ml of tissue solubilized TS-2. The vials were incubated for 2–4 hr at 50° C., mixed with 250 μl of 10% glacial acetic acid, after mixing, 18 ml of 3a70B scintillation cocktail was added. The vial was again swirled and left overnight to diminish chemiluminescence. The radioactivity level was counted using Beckman liquid scintillation counter.

The above results show that oligonucleotides SEQ. ID NOs.:6 and 8 have increased in vivo stability compared to oligonucleotide SEQ. ID NO.:1 and that the increase in stability of oligonucleotides SEQ. ID NOs.:6 and 8 is the result of formation of intramolecular pseudo-cyclic structures under physiological conditions as well as protection of 3'-end by 3'-3'-linkage. We undertook a preliminary pharmacokinetic tissue disposition study of oligonucleotide SEQ. ID NO.:8 in mice. We administered 2 mg/kg of oligonucleotide SEQ. ID NO.:8 (a mixture of $^{35}$S-labeled and unlabeled oligonucleotide) subcutaneously to mice to understand if there are any significant differences in pharmacokinetic and tissue distribution profiles compared to PS-oligonucleotides in general. At 3, 48, and 96 hr after administration, mice were sacrificed and liver, kidney, heart, lung, and spleen were collected. Tissues were homogenized and radioactivity levels were quantitated.

Figure 6A:
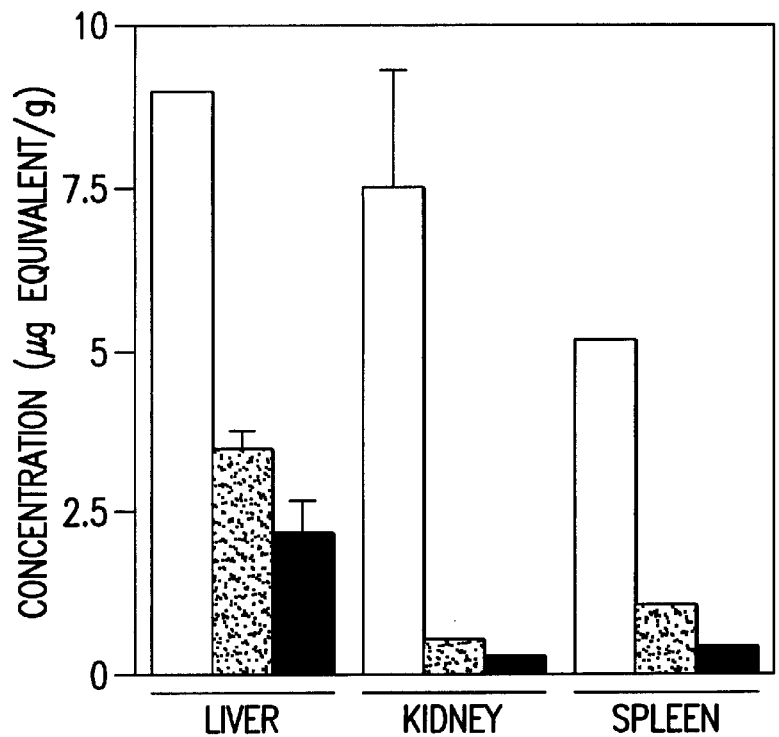
FIGS. 6A, 6B, and 6C show tissue disposition (FIGS. 6A and 6B) and elimination in urine (FIG. 6C) of oligonucleotide SEQ. ID NO.:8 following subcutaneous administration to mice.
Figure 6B:
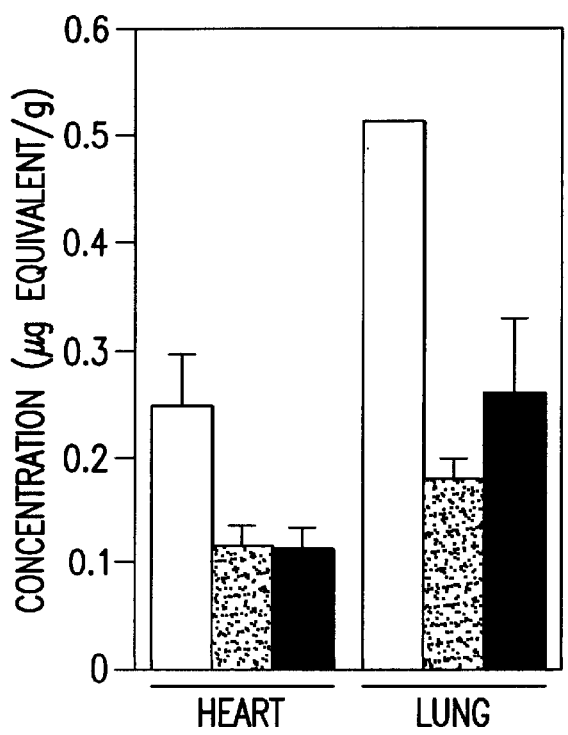
Figure 6C:
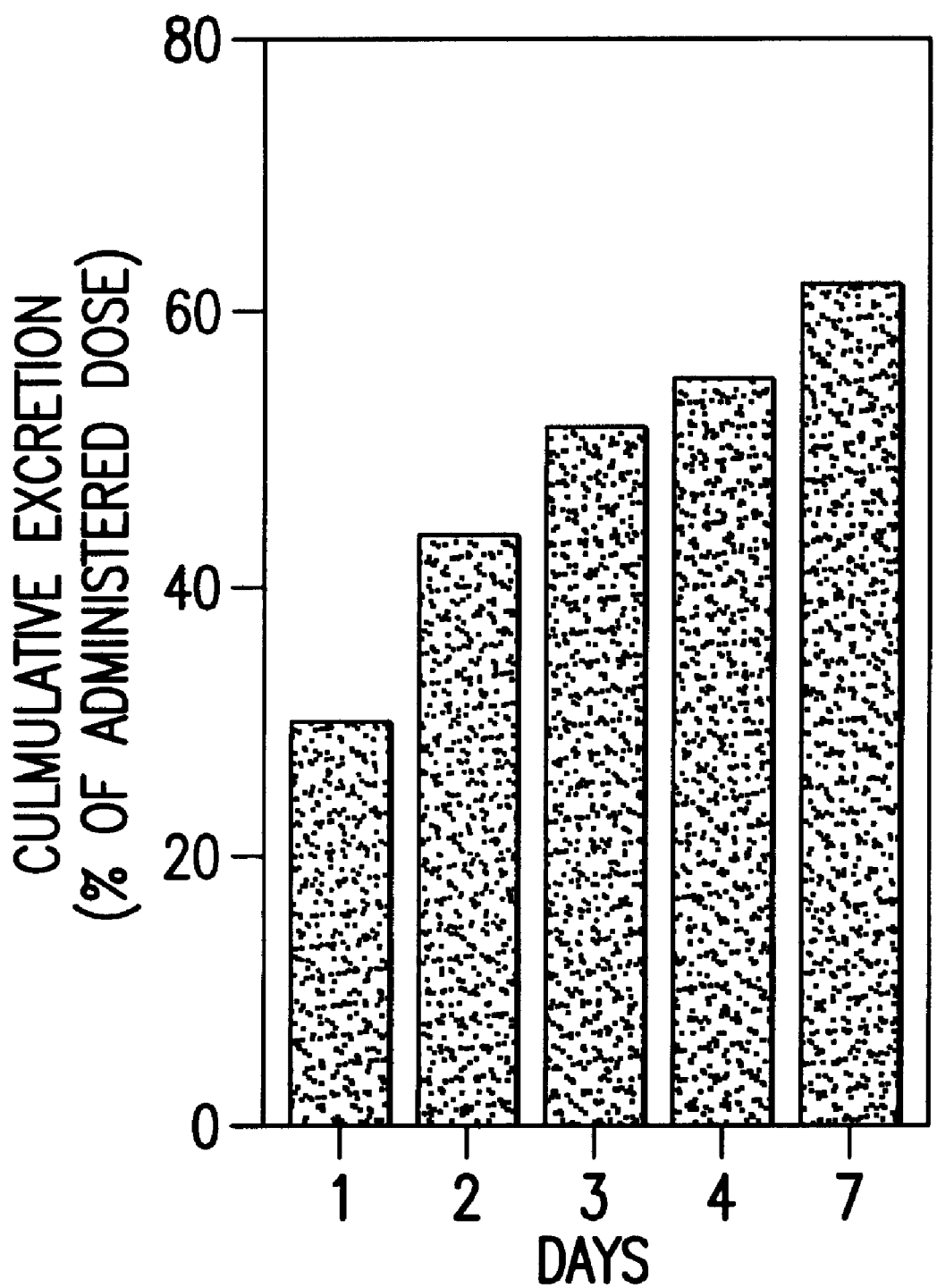

Concentration of oligonucleotide SEQ. ID NO.:8 based on the radioactivity levels in tissues is presented in FIG. 6A and B. It shows that oligonucleotide SEQ. ID NO.:8 was distributed to major organs and the tissue disposition profile was similar to what has been reported for other PS-oligonucleotides (36–39). However, notable changes were observed in clearance from the tissues compared with PS-oligonucleotides (16,17,19,36). FIG. 6A shows the percent of the administered dose distributed to liver, kidney, and spleen at 3, 48, and 96 hr. FIG. 6C shows more than 60% of the administered dose was excreted in urine in 7 days. Clearance of oligonucleotide from tissues was more rapid than what has been generally observed with PS-oligonucleotides in general (16,17,19,36). This observation suggest that oligonucleotide SEQ. ID NO.:8 remains in the intramolecular pseudo-cyclic form in these tissues, interacts less with macromolecules, and is thereby rapidly eliminated from these tissues.

Example 8

Inhibition of Cell Growth

Having established that these oligonucleotides formed intramolecular pseudo-cyclic structures under physiological conditions and adopted a linear form and bound to the target in the presence of the complementary RNA, we performed further experiments to determine if the pseudo-cyclic structures would be taken up by cell, bind to the mRNA, and ultimately exert biological activity similar to that of oligonucleotide SEQ. ID NO.:1, which does not have a protective segment appendage and also does not form any intramolecular structures. Studies were carried out using oligonucleotides SEQ. ID NOs.:1 and 7–9 to examine inhibition of cancer cell growth of MDA-MB 468 (breast cancer) and GEO (colon cancer) cell lines using anchorage-dependent and anchorage-independent assays. In the assay system described below, use of lipids is not required for delivery of oligonucleotides. Avoidance of the use of lipids was desired because PCOs have variable polyanionic natures, and their encapsulation with lipids may not be consistent.

Cell culture. MDA-MB-468 human breast cancer cells were procured from the American Type Culture Collection (Rockville, Md.). The cells were routinely maintained in a 1:1 (v/v) mixture of Dulbecco's Modified Eagle's medium (DMEM) and Ham's F12 medium supplemented with 10% heat-inactivated fetal calf serum, 20 mM Hepes (pH 7.4 ), penicillin (100 U/ml), and streptomycin (100 μg/ml) (Flow, Irvine, UK). GEO cells were kindly provided by Dr. M. Brattain (Baylor College of Medicine, Houston, Tex.). GEO cells were maintained in McCoy's medium supplemented with 10% heat-inactivated fetal bovine serum, 20 mM Hepes (pH 7.4), penicillin (100 U/ml), and streptomycin (100 μg/ml) in a humidified atmosphere of 95% air and 5% $CO_2$ at 37° C.

Anchorage-dependent growth assay. MDA-MB-468 cells ($10^4$ cells/well) were seeded into 48-multiwell cluster dishes (Becton Dickinson, Milan, Italy), and treated every 24 hr with the indicated concentrations of oligonucleotides. After 5 days of growth, the cells were trypsinized and counted with an hemocytometer.

Clonogenic assay. GEO cells ($5 \times 10^3$ cells/well) were seeded in 0.3% Difco Bactoagar (Difco, Detroit, Mich.) supplemented with complete culture. This suspension was layered over 0.5 m; of 0.8% agar-medium base layer in 24-multiwell cluster dishes (Becton Dickinson, Milan, Italy). After 12 days, the colonies were stained with nitroblue tetrazolium, and colonies larger than 50 μm were counted with an Artek 880 colony counter (Artek Systems, Farmingdale, N.Y.).

Figure 4A:
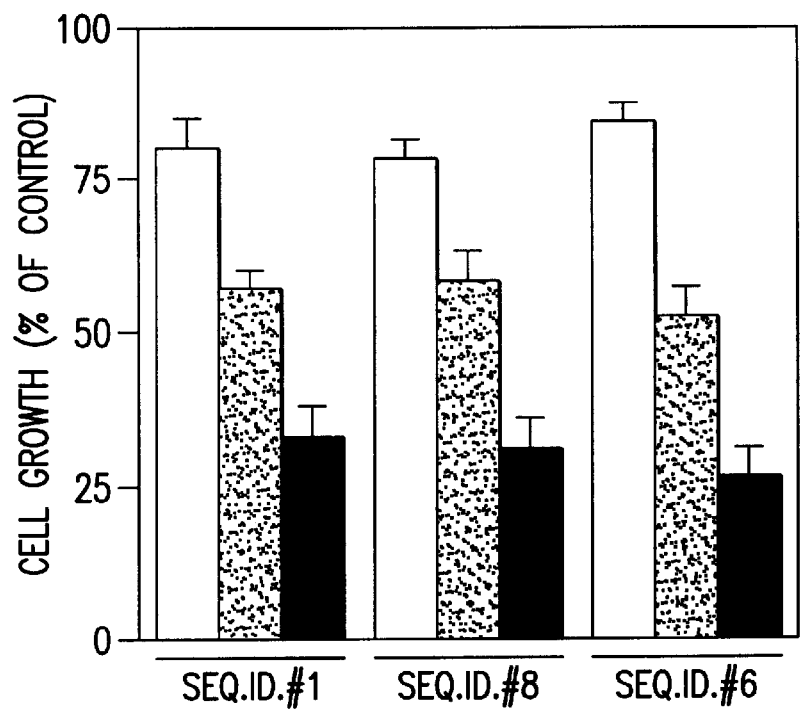
FIGS. 4A and 4B show inhibition of anchorage-independent growth of GEO cancer cells (FIG. 4A) and anchorage-dependent growth of MDA-MB-468 cancer cells by oligonucleotides SEQ. ID NOs.: 1, 8, and 6 at 0.2 $\mu$M (no shade bars), 0.5 $\mu$M (light shaded bars), and 1.0 $\mu$M (dark shaded bars) (FIG. 4B).
Figure 4B:
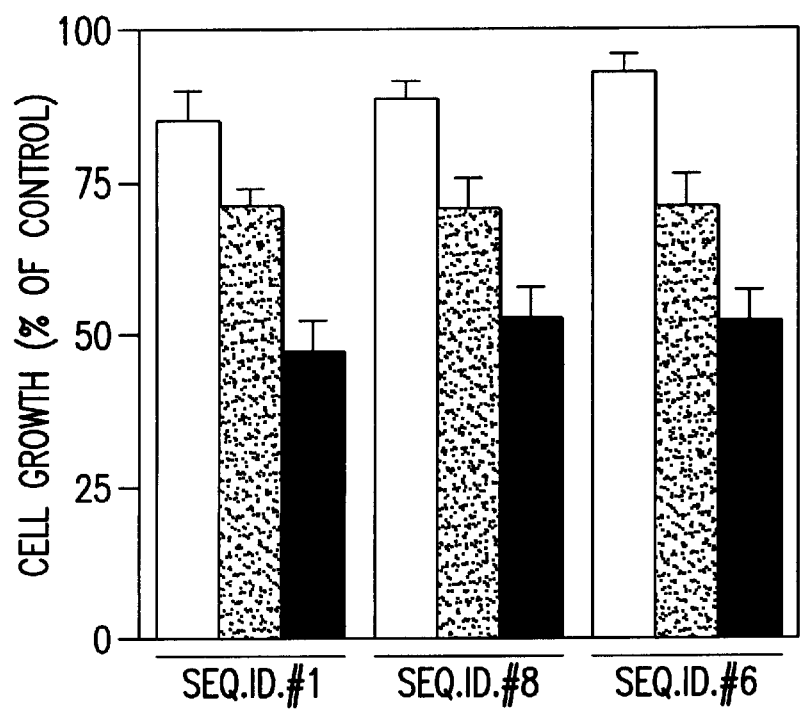

Oligonucleotide SEQ. ID NO.:1 has been extensively studied against a number of cancer cell lines and has been shown to inhibit cell growth by an antisense mechanism (7,32,33). Results of percent growth inhibition using these oligonucleotides is summarized in FIG. 4. All oligonucleotides showed similar dose-dependent growth inhibitory activity. These results confirm that oligonucleotides SEQ. ID NOs.:7–9, which have same antisense sequence as that of oligonucleotide SEQ. ID NO.:1, had similar cell growth inhibitory activity and that the protective segment portion of oligonucleotides SEQ. ID NOs.:7–9 did not interfere in their biological activity. Future studies will focus on exploring non-sequence-specific activities, if any, of the protective segment portion with appropriate controls.

Example 9

Fluorophore Labeled Cyclicons

Cyclicon Design and Synthesis

The cyclicons were designed to contain a long primer-probe and a short modifier oligo attached through a 3'-3' or 5'-5' linkage. The primer-probe studied herein was a twenty nucleotide-long sequence that was complementary to a portion of the human MDM2 mRNA. The modifier oligo was complementary to six to eight nucleotides at the 3'- or 5'-end of the primer-probe sequence. If the modifier oligo was complementary to the 5'-end of the primer-probe, the two oligos were attached through a 3'-3' linkage. If the modifier oligo was complementary to the 3'-end of the primer-probe, the two oligos were attached through a 5'-5' linkage.

Fluorescent Cyclicon Probe Design

To detect the hybridization between the probe sequence of cyclicon and the target nucleic acid, a fluorophore (fluorescein) or fluorescence resonance energy donor (FRED) was attached to the free end (3'- or 5'-) of the modifier oligo. A fluorescence quencher (DABCYL) or fluorescence resonance energy acceptor (FREA) on a thymine base (at 5-position) was incorporated in the primer-probe sequence (FIG. 8). In the absence of the target nucleic acid, cyclicons form intramolecular cyclic structures; in this state, the fluorophore and the quencher are brought in close proximity to each other (FIG. 8), resulting in the loss of fluorescence because of FRET. In the presence of a target nucleic acid sequence in solution, the probe sequence hybridizes to the complementary sequence on the target,. destabilizing the intramolecular cyclic structure and causing it to open up, resulting in spontaneous fluorescence emission. The presence of fluorescence indicates hybridization between the target nucleic acid and the probe sequence of the cyclicon (FIG. 8).

Synthesis

3'-3' and 5'-5' linked cyclicons were synthesized on a 1 to 2 μmol scale on a Biosearch 8900 DNA synthesizer as described earlier (45–47), using 3'- and 5'-phosphoramidites as required. The 5'-phosphoramidites, 6-FAM phosphoramidite, 6-FAM-CPG, DABCYL-T phosphoramidite, and DABCYL-CPG were obtained from Glen Research Corporation. Deoxynucleoside-3'-phosphoramidites were obtained from Perkin-Elmer. After the synthesis, oligonucleotides were deprotected with concentrated ammonium hydroxide and purified on non-denaturing polyacrylamide gels. After excision and extraction of the appropriate full-length oligonucleotide band from the gels, they were desalted using Waters $C_{18}$ Sep-Pack cartridges. The oligonucleotides were dried in a Speed-Vac under vacuum and the concentrations were determined by absorbance measurement at 260 nm. The oligonucleotide sequences synthesized and used in the subsequent Examples are:

Oligonucleotide 12 (SEQ. ID. No.:12)
5'-TGACACCT(Q)GTTCTCACTCAC-3'-3'-ACTGTG-F; (+364 to +383)

Oligonucleotide 13 (SEQ. ID. NO.: 13)
5'-TGACACCTGT(Q)TCTCACTCAC-3'-3'-ACTGTGGA-F;

Oligonucleotide 14 (SEQ. ID. NO.: 14)
3'-CACTCACT(Q)CTTGTCCACAGT-5'-5'-GTGAGT-F;

Oligonucleotide 15 (SEQ ID NO.:15)
3'-CACTCACTCT(Q)TGTCCACAGT-5'-5'-GTGAGTGA-F all of which are cyclicons (Q and F stand for quencher DABCYL and fluorophore fluorescein);

Oligonucleotide 16 (SEQ. ID. No.: 16)
DNA target:
5'-ATCTGTGAGTGAGAACAGGTGTCACCTT-3'

Fluorescent Measurements

Fluorescent measurements were carried out in Perkin-Elmer's ABI Prism 7700 machine in plate-read mode in a 96-well plate. Each sample was 50 μL. All the reactions were carried out in 50 mM Tris, pH 8.0, containing 1 mM $MgCl_2$.

DNA Polymerase Chain Extension

The 40-mer template (SEQ. ID. No.: 17 3'-TTCCACTGTGGACAAGAGTGAGTGT CTACATGGACCCAGG-5') (0.15 $A_{260}$ units) was mixed with 5'-$^{32}$P-end labeled primers (0.08 $A_{260}$ units) in 16 μL of 50 mM KCl, 1.5 mM $MgCl_2$, 10 mM Tri-HCl, pH 9.0. The samples were heated to 95 ° C. for 5 min and cooled to room temperature for 15 min before lyophylization. In a final volume of 30 μL, the annealed template/primers were then incubated for 3 hr at 37° C. with 5 units of Taq DNA polymerase (Amersham Pharmacia), 200 μM dNTPs (Perkin-Elmer), 50 mM KCl, 1.5 mM $MgCl_2$, 10 mM Tris-HCl, pH 9.0. The extension products were fractionated by 15% denaturing PAGE and visualized by autoradiography.

RT-PCR

MDM2 mRNA was extracted from JAR cells as described (45) and used in the PCR reactions. All the PCR reagents were purchased from PE-BioSystems, CA. The TaqMan primers and probes used are 3'-GACTAACTGATGATGGTTCAAGGACA-5' (SEQ ID. NO.: 18, forward primer; +311 to +366), 3'-CACTCTTGTCCACAGTGGAACT-5', SEQ. ID NO.19, reverse primer; +368 to +389) 3'-TAMRATCCTTAGTAGCCTGAGTCCATGTAGA CAC-6-FAM-5' (SEQ. ID NO.20 probe; +338 to +389) and 3'-CATGTTCTCGAAGTCCTTCTC-5' (SEQ. ID NO:21 reverse primer-2; +415 to +435). Typically each reaction was carried out in a final volume of 200 µL containing 1×TaqMan EZ buffer, 3 mM manganese, 300 µM each of dATP, dCTP, and dGTP, 600 µM dUTP, 200 nM each of forward and reverse primers, 100 nM TaqMan probe, 0.1 U/µL rTth DNA polymerase, 0.01 U/µL AmpErase UNG and 1 to 50 ng of template RNA. In reactions where the TaqMan probe and reverse primer are were replaced with 5'-5'-attached cyclicon, the final concentration of cyclicon was 300 nM. All the RT-PCR reactions were carried out in triplicate (50 µL each). Amplification was performed in Perkin-Elmer's ABI Prism 7700 Sequence Detection System. The thermal cycling parameters were—an initial 2-min hold at 50° C. and 30-min hold at 60° C., a deactivation hold of 5 min at 95° C., followed by 38 to 40 cycles of a 20-sec denaturation step at 94° C. and a 1-min anneal/extension step at 60° C.

Cyclicon Structure

Formation of intramolecular cyclic structures by cyclicons was examined by incubating a small amount (~20 nM) of fluorescent cyclicon with increasing concentrations (up to 1:1000 ratio) of the same cyclicon synthesized without fluorescent and quencher tags, and measuring the fluorescence. If the cyclicons formed intermolecular linear or cyclic structures, a fluorescence signal should appear as a result of excess non-fluorescent cyclicon in solution (FIG. 9). We attached the quencher at the 5-position of thymine in the present study; these molecules can also be attached on at other positions, including the 2'-position of a sugar moiety (48). FIG. 9 shows that the increase in fluorescence as a result with increasing concentrations of non-fluorescent cyclicon is minimal. When a large excess of target DNA over non-fluorescent cyclicon was added to the same solution, however, full fluorescence was detected (FIG. 9B). These results suggest that cyclicons exist in intramolecular cyclic structure form in the absence of the target sequence. In addition, concentration-dependent UV thermal melting studies of cyclicons alone showed $T_m$s within ±1.0° C., suggesting intramolecular cyclic structure formation in the absence of the target sequence (data not shown).

3'-3' vs. 5'-5' Linkage in Cyclicons

The quencher is incorporated in the probe sequence in such a way that when the cyclic structure is formed, the fluorophore comes close to the FREA and the fluorescence is quenched completely. Examination of the fluorescence of oligonucleotides 12–15 (SEQ ID NOs.:12–15) alone showed that 3'-3' attached oligonucleotides 12 (SEQ ID NO.:12) and 13 (SEQ ID NO.:13) have had higher background fluorescence than 5'-5' attached oligonucleotides 14 (SEQ ID NO.:14) and 15 (SEQ ID NO.:15). This difference could reflect the greater distance between the fluorophore and quencher in 3'-3' attached cyclicons as a result of 3'-skewing of the two strands of duplex DNA. It would be appropriate not to skip a base between the fluorophore and quencher in 3'-3' attached cyclicons to reduce background fluorescence. The optimum distance between the FRED and FREA molecules would be about 70 to 100 Å to disrupt the FRET and attain full fluorescence (49, 50). We maintained a distance of about nineteen internucleotide phosphate bridges between the donor and acceptor molecules. When the cyclicon hybridizes to the target nucleic acid sequence, the FRED and FREA molecules are pulled apart about 70 Å, effectively diminishing FRET between the molecules and resulting in spontaneous fluorescence emission. The linkage between the probe and the short oligos can be either 3'-3' or 5'-5' as required for the application of the cyclicon. For example, for use in cellular studies, a 3'-3' linkage would be more appropriate because of the higher stability of the 3'-3'-attached oligonucleotides against nucleases in in vitro and in vivo studies (45), whereas for a primer in PCR reactions, a free 3'-end containing 5'-5' attached cyclicon is more appropriate.

Specificity of Hybridization of Cyclicons to Target Nucleic Acid

Figure 12:
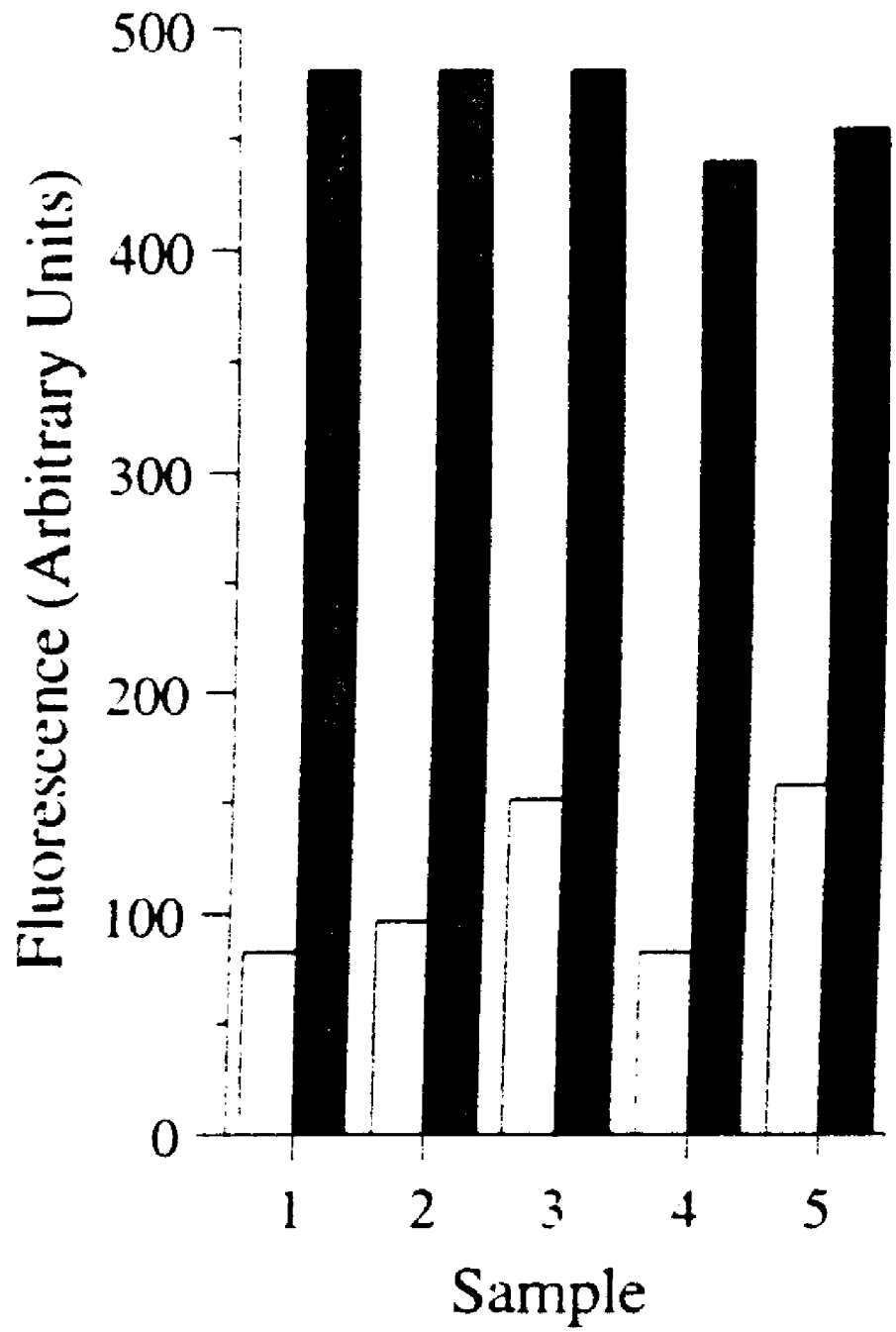
FIG. 12 displays the sequence-specificity of cyclicons; it shows oligonucleotide 13 (SEQ ID NO.:13) (20 $\mu$M) in the absence (white bars) and presence (shaded bars) of DNA target (50 nM).

To determine the specificity of cyclicons, a synthetic mixture containing one to eight different oligonucleotide sequences (20 to 24-mers) was made up and mixed with cyclicons in the absence and presence of perfectly complementary target DNA. Oligonucleotide 2 (20 nM) in the absence (white bars in FIG. 12) and presence (shaded bars in FIG. 12) of DNA target (50 nM). In sample 1 no other non-specific oligonucleotides were added. In sample 2 a 20-mer random oligonucleotide sequence (1 µM) was added. In sample 3 two 20-mer oligonucleotides (1 µM) that did not have any complementarity to the cyclicon were added. In sample 4, four 20-mer oligonucleotides (2 µM) that did not have any complementarity to the cyclicon were added. In sample 5 eight 20-mer oligonucleotides (2 µM) that did not have any complementarity to the cyclicon were added. FIG. 12 shows that in the absence of a matched target DNA, cyclicons showed no or little fluorescence. When the perfectly matched target DNA strand was added to the same solution, fluorescence was detected, suggesting that the intramolecular cyclic structure of the cyclicon was opened up in the presence of target nucleic acid but not in the presence of non-targeted nucleic acid sequences.

Effect of the Presence and Position of Dabcyl on Primer Extension

Figures 11A, 11B:
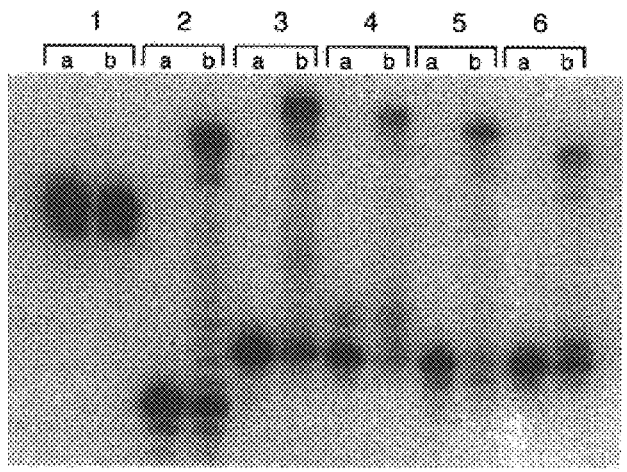
FIG. 11A displays an autoradiogram showing DNA polymerase chain extension on the 40-mer template using different primers containing DABCYL (*) at different position on the primers. The lane numbers shown on top of the gel correspond to the primer number given below the gel. The lanes noted 1 (containing oligonucleotide 12 (SEQ ID NO.:12)) show no extension. The labels a and b represent reaction mixture before and after extension, respectively.
FIG. 11B shows the sequences of the different primers used and the dashed lines represent the resulting primer extension products. The asterix (*) represents the location of DABCYL in the sequence.

To determine if the presence of quencher on a thymine of the primer would interfere with Taq polymerase extension, we have synthesized four 20-mer oligodeoxynucleotides with DABCYL-thymine at nucleotide positions 2, 3, 5, and 7 from the 3'-end and compared the primer chain extension with that of a primer without DABCYL. FIG. 11 shows the Taq-polymerase extension products in the presence of each primer. These results show that all the five oligos served as primers, suggesting that the presence of DABCYL in the primer did not interfere with the chain extension activity of polymerase. This allows the flexibility to incorporate the quencher in the sequence at appropriate sites.

Detection and Quantitation of Target Nucleic Acid with Cyclicons

Figure 10A:
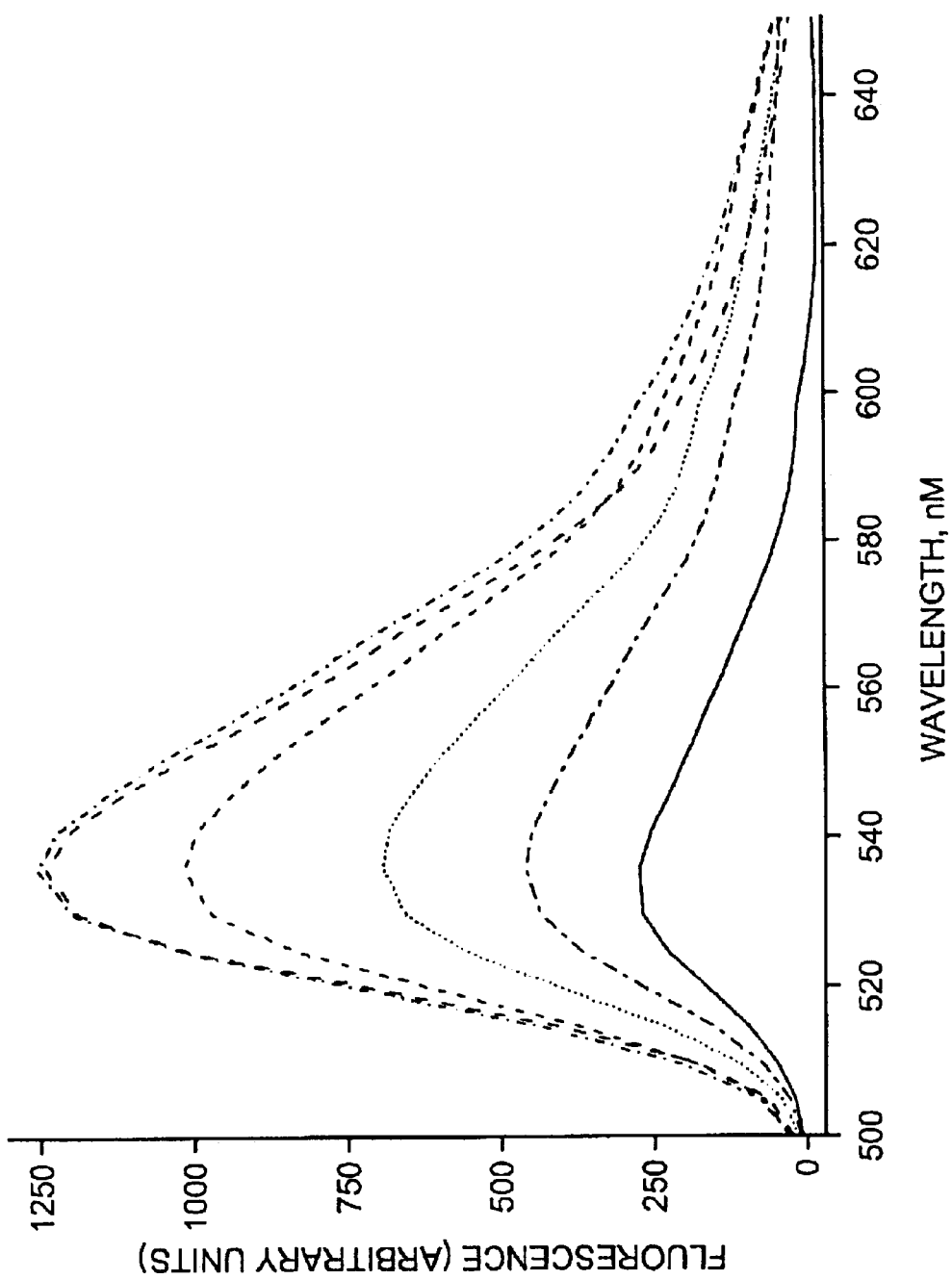
FIG. 10A displays fluorescence spectra of oligonucleotide 12, (SEQ. ID NO.:12) alone and in the presence of different concentrations of complementary oligodeoxynucleotide as determined by ABI Prism 7700 Sequence Detection System in palteread mode.
Figure 10B:
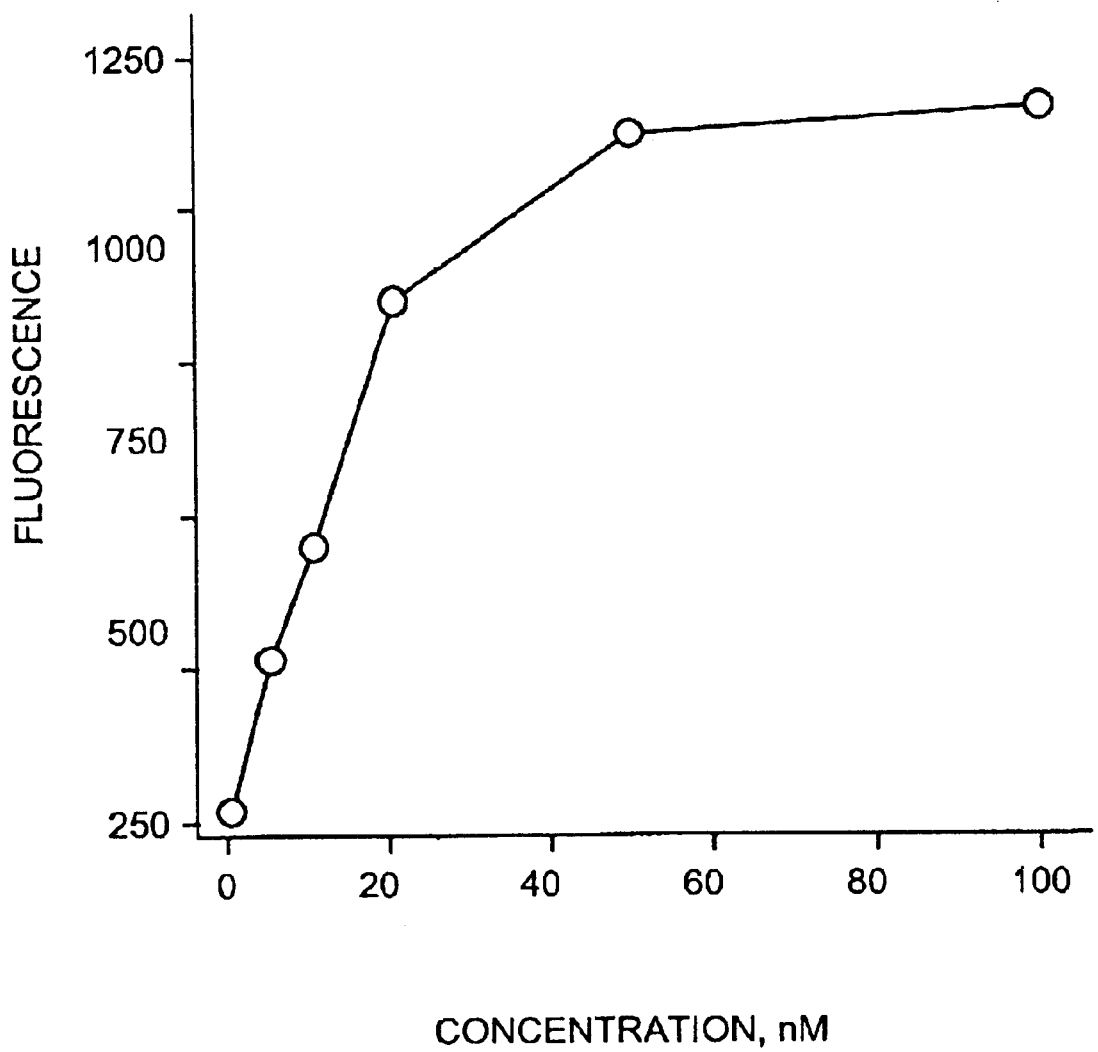
FIG. 10B shows a linear increase in fluorescence as a function of target concentration.

We monitored hybridization of the cyclicon with the target nucleic acid and measured the fluorescence increase as a function of target nucleic acid concentration. FIG. 10 shows fluorescence spectra of oligonucleotide 12 (SEQ ID NO.:12) in the absence and presence of DNA target nucleic acid strand as determined by ABI Prism 7700 Sequence Detector in the plate-read mode. The background fluorescence in the absence of target was the result of the greater distance between the fluorophore and quencher in 3'-3' linked cyclicons. The addition of DNA target strand to the solution increased fluorescence as a result of hybridization of the cyclicon probe sequence to the target nucleic acid strand and opening up of the intramolecular cyclic structure (FIG. 10). The linear increase in fluorescence with the increase in target concentration (FIG. 10B) suggests that the method can be used for quantitative detection of the target nucleic acid sequence in solution.

To verify if full fluorescence was emitted upon hybridization of cyclicon to the target nucleic acid, cyclicons alone and in the presence of the target DNA were treated with DNase I and the fluorescence was measured (data not shown). The fluorescence readings were within ±10% of those observed without DNase I treatment in the presence of target nucleic acid, suggesting that full fluorescence was emitted upon hybridization of the cyclicon to the target nucleic acid under study.

Figures 13A, 13B:
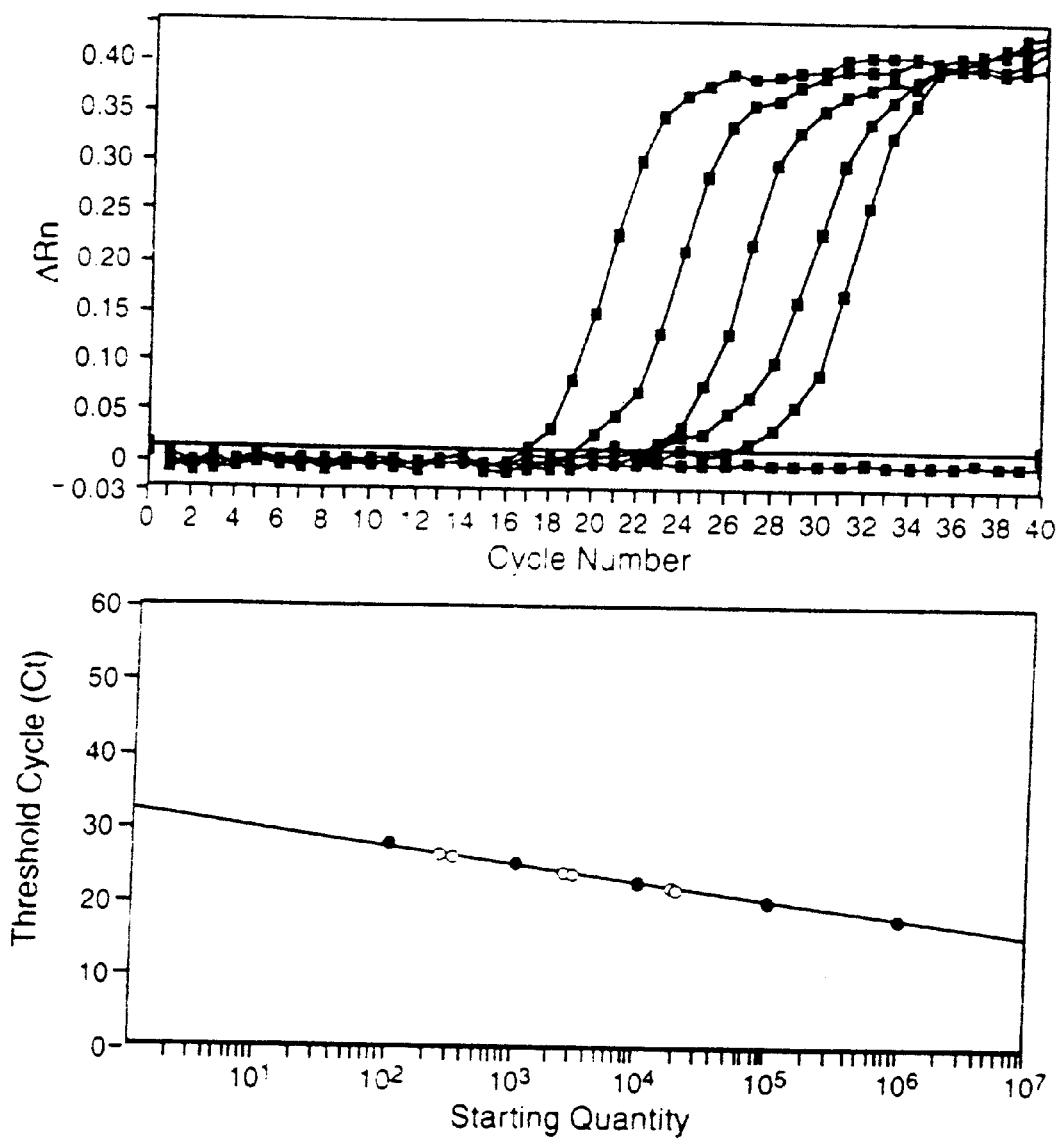
FIG. 13B displays real-time quantitative RT-PCR amplification plots, ΔRn versus cycle number, for known amounts of MDM2 mRNA extracted from JAR cells using oligonucleotide 14 (SEQ ID NO.:14) as a reverse primer-probe. Buffer and no template control plots are at the base line. This data was used to construct the standard curve displayed in FIG. 13A, which can subsequently be used for the determination of mRNA levels in unknown samples.

To further examine the applicability of cyclicon primer-probe for the determination of mRNA levels in unknown samples by real-time quantitative RT-PCR, we have constructed a standard curve with known amounts of MDM2 mRNA extracted from JAR cells (FIG. 13) using oligonucleotide 14 (SEQ ID NO.:14) as a reverse primer-probe. The standard curve shown in FIG. 13 suggests that the method could be applicable for accurate measurement of MDM2 mRNA in unknown samples.

Cyclicons as Unimolecular Primer-probes in Real-time PCR Amplification

Figure 14:
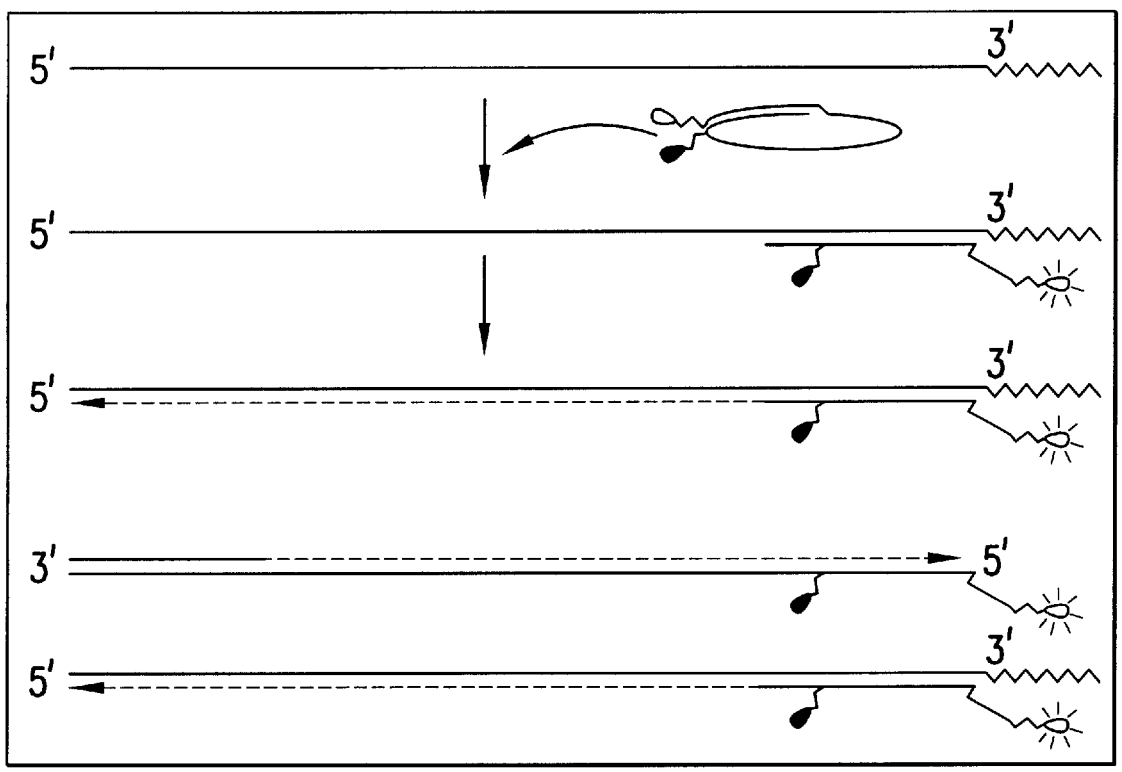
FIG. 14 is a representation of polymerase chain extension with a $5'$-$5'$-attached cyclicon as a primer-probe in RT-PCR. Lines with zig-zag ends represent RNA template strand that requires amplification. Short, solid lines represent forward and reverse primers. Dotted lines represent chain elongation and its direction.

The 5'-5' attached cyclicon can be used as an unimolecular primer-probe to monitor real-time RT-PCR amplification (FIG. 14). We performed RT-PCR of MDM2 RNA extracted from JAR cells as above. We compared the amplification results obtained with TaqMan primers and probe with those of cyclicon-primer-probe. In these experiments, the forward primer was the same in both the reactions and the bimolecular TaqMan reverse primer and probe were replaced with an unimolecular 5'-5'-attached cyclicon primer-probe.

The 5'-5'-attached cyclicon had two 3'-ends. Only the primer-probe oligo segment was complementary to the MDM2 RNA and this 3'-end was extended when it recognized and hybridized to the RNA in the first round of RT-PCR. The 3'-end of the modifier oligo was not extendible, because the modifier oligo did not bind to the RNA, and its 3'-end was blocked by fluorescein moiety.

Figure 15:
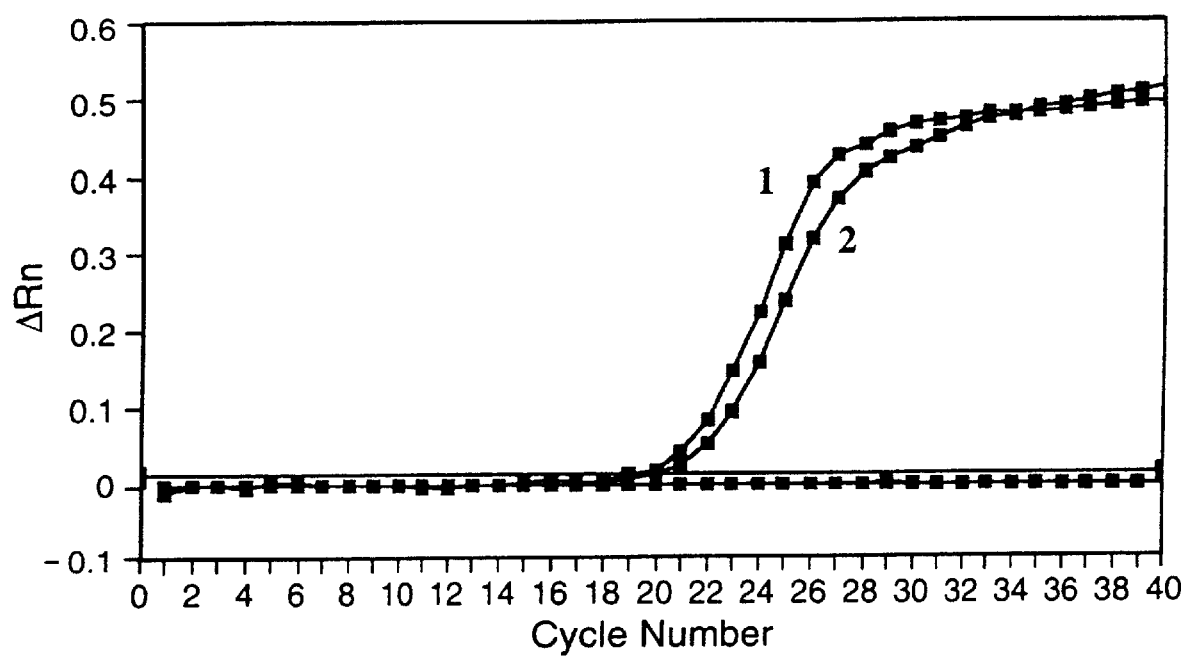
FIG. 15 displays real-time amplification plots, ΔRn versus cycle number, for MDM2 mRNA extracted from JAR cells using oligonucleotide 14 (SEQ ID NO.:14) as reverse primer-probe (curve 1), and TaqMan primers and probe (curve 2). Buffer and no template control plots are at the base line.

The results of the RT-PCR amplification of MDM2 RNA by TaqMan primers and probe, and cyclicon are shown in FIG. 15. These plots suggest that the 5'-5'-attached cyclicon served as an efficient unimolecular primer-probe. In order to examine the amplification product, we labeled the 5'-end of each product from the PCR reactions with $^{32}$P and analyzed them by denaturing PAGE. The results showed the presence of expected length amplification product in which cyclicon was used as primer probe as was the case with TaqMan primer (data not shown).

Mechanism of Signaling

Figure 16A:
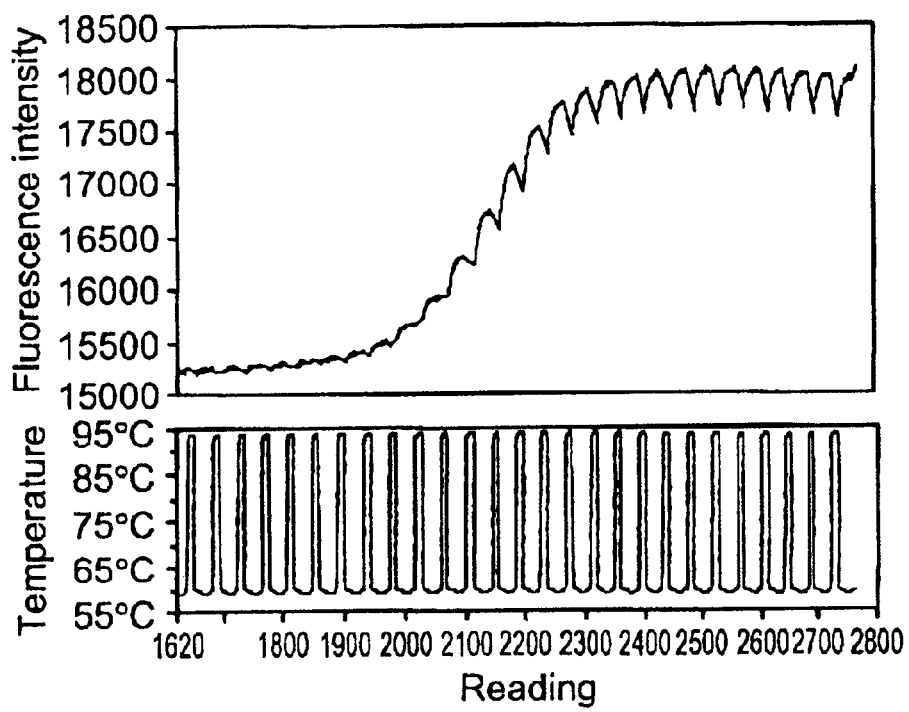
FIG. 16 displays plots showing change in fluorescence pattern during amplification in each cycle with TaqMan probe (FIG. 16B) and oligonucleotide 14 (SEQ ID NO.:14) (FIG. 16A).
Figure 16B:
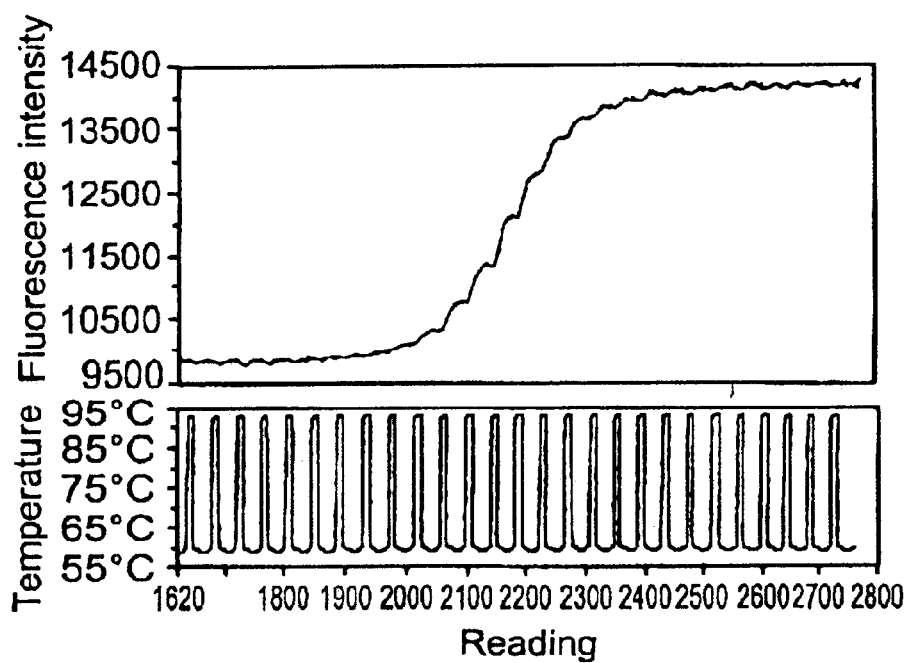
Figure 17:
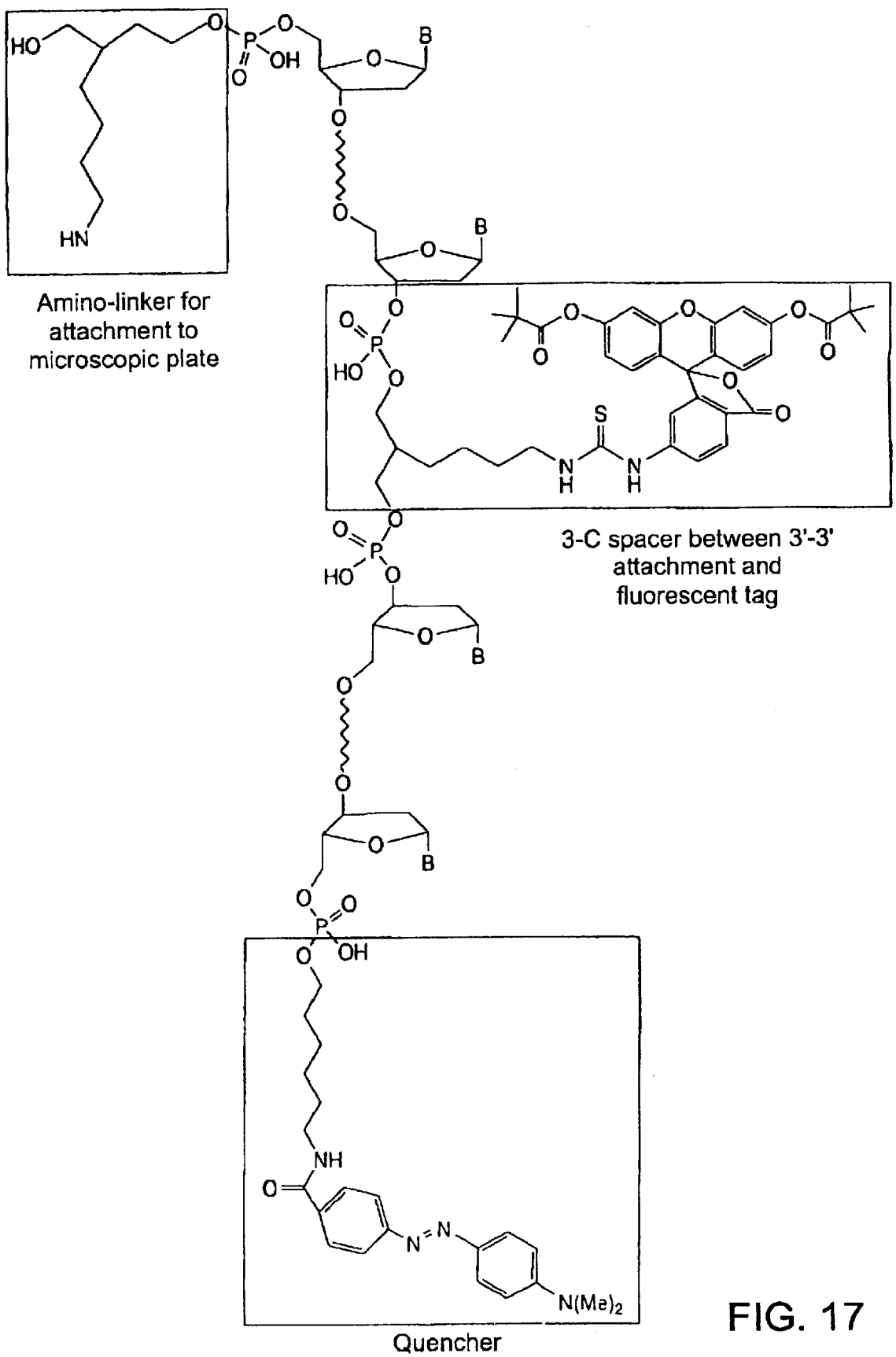
FIG. 17 displays an example of the chemical structure of a cyclicon according to the invention adapted for attachment to a solid support.
Figure 18:
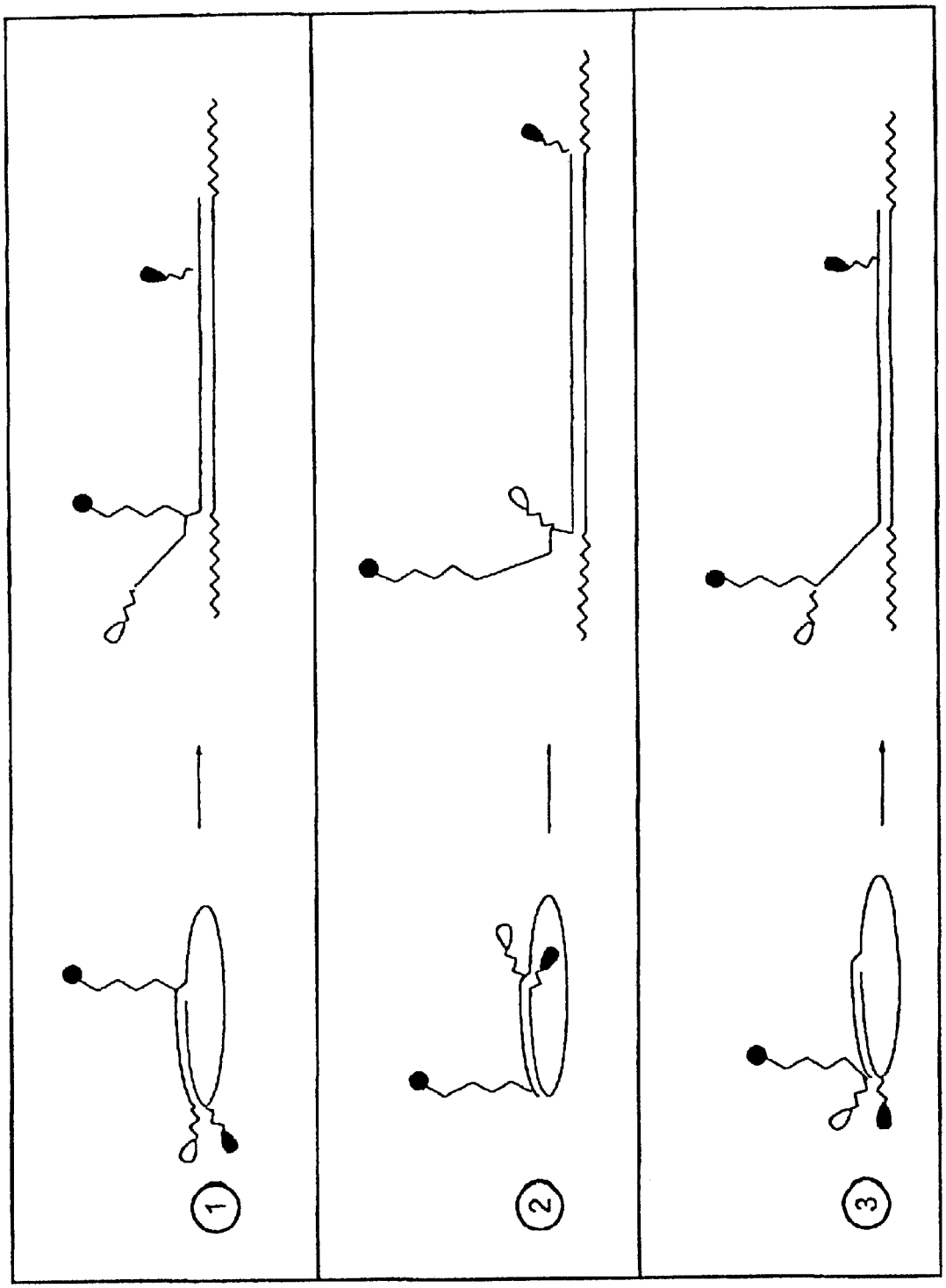
FIG. 18 displays three configurations for a cyclicon attached to a solid support (represented by the solid black circle).

To examine the mechanisms of fluorescence signaling by cyclicon during PCR cycles we plotted the fluorescence signal for PCR cycles 14 through 40 for both the TaqMan probe and cyclicon (FIG. 16). As expected, the signaling mechanisms were different for the two probes and they showed different characteristics. As seen in FIG. 9A, the TaqMan probe registered an increase in fluorescence signal with amplification and never showed a decrease in fluorescence signal as expected. In contrast, the cyclicon gave an increase in the fluorescence signal with amplification and a lower fluorescence signal during the 60° C. hold.

ADDITIONAL REFERENCES

1. Agrawal (1996) *Trends Biotech.,* 14, 376–387.
2. Ciba Foundation Symposium. (1997) *Oligonucleotides as Therapeutic Agents;* John Wiley, New York.
3. Agrawal and Zhao (1998) *Cur. Opn. Chem. Biol.,* 2, 519–528.
4. Agrawal. (1996) *Antisense Therapeutics,* Humana Press, New Jersey.
5. Crooke. (1998) *Antisense Research and Application,* Springer, New York.
6. Chen et al. (1998) *Proc. Natl. Acad. Sci. USA,* 95, 195–200.
7. Cho-Chung et al (1997) *Antisense Nucleic Acid Drug Dev.,* 7, 217–223.
8. Akhtar. and Agrawal (1997) *Trends Pharmaceutical Sci.,* 18, 12–18.
9. Bennett (1998) *Biochem. Pharmacol.,* 55, 9–19.
10. Dean and McKay (1994) *Proc. Natl. Acad. Sci. USA.,* 91, 11762–11766.
11. Zhao et al. (1997) *Antisense Nucleic Acid Drug Dev.,* 7, 495–502.
12. Agrawal et al. (1997) *Antisense Nucleic Acids Drug Dev.,* 7, 575–584.
13. Schechter and. Martin, R. R. (1998) In Crooke, S. T. (ed), *Antisense Research and Applications.* Springer, New York, pp. 233–241.
14. Henry et al. (1997) *Anti-Cancer Drug Des.,* 12, 395–408.
15. Srinivasan and Iversen (1995) *J. Clin. Lab. Anal.,* 9, 129–137.
16. Agrawal et al. (1995) *Clin. Pharmacokin.,*28, 7–16.
17. Grindel et al. (1998) *Antisense Nucleic Acids Drug Dev.,* 8, 43–52.
18. Zhang et al. (1995) *Clin. Pharm. Expt. Ther.,* 58, 44–53.
19. Nicklin et al (1998) In Crooke,S. T. (ed), *Antisense Research and Applications.* Springer, New York, pp. 141–168.
20. Metelev et al. (1994) *Bioorg. Med. Chem. Lett.,* 4, 2929–2934.
21. Agrawal et al. (1997) *Proc. Natl. Acad. Sci. USA,* 94, 2620–2625.
22. Kandimnalla et al. (1995) *Nucleosides and Nucleotides,* 14, 1031–1035.
23. Kandimalla et al. (1997) *Nucleic Acids Res.,* 25, 370–378.
24. Shen et al. (1998) *Bioorg. Med. Chem.,* 6, 1695–1705.
25. Agrawal and Zhao (1998) *Antisense Nucleic Acids Drug Dev.,* 8, 135–139.
26. Altman et al. (1996) *Chimia,* 50, 168-.
27. Nicklin et al. (1997) *Nucleosides and Nucleotides,* 16, 1145–1153.
28. Tang et al. (1993) *Nucleic Acids Res.,* 21, 2729–2735.
29. Agrawal et al. (1995) In Akhtar,S. (ed), *Delivery Stratagies for Antisense Oligonucleotide Therapeutics.* CRC Press, Boca Raton, Fla.,pp 105–121.
30. Zhang et al. (1995) *Clin. Chem.,* 41, 836–843.
31. Abe et al. (1998) *FEBS Lett.,* 425, 91–96.
32. Srivastava et al. (1998) *Breast Cancer Res. Treat.,* 49, 97–107.
33. Nesterova and Cho-Chung (1995) *Nature Med.,* 1, 528–533.
34. Agrawal and Iyer (1997) In Schlingensiepen, R. and Schlingensiepen, W. B. K.-H. (eds), *Antisense—From Technology to Therapy,* Blackwell Sciences, Berlin, Germany, pp 59–77.
35. Temsamani et al. (1997) *Antisense Nucleic Acids Drug Dev.,* 7, 159–165.
36. Agrawal et al. (1991) *Proc. Natl. Acad. Sci. USA,* 88, 7595–7599.
37. Zhang et al. (1995) *Biochem. Pharmacol.,* 49, 929–939.
38. Sands et al. (1994) *Mol. Pharmacol.,* 45, 932–943.

39. Orr et al. (1997) *Nucleosides and Nucleotides,* 16, 1699–1702.
40. Holland et al. (1991) Proc. Natl. Acad. Sci. USA, 88, 7276–7280.
41. Lie et al. (1998) J. Cur. Opn. Biotech., 9, 43–48.
42. Tyagi et al. (1996) Nat. Biotechnol., 14, 303–308.
43. Nazarenko et al. (1997) Nucleic Acids Res., 25, 2516–2521.
44. Whitcombe et al. (1999) Nat. Biotechnol., 17, 804–807.
45. Jiang et al. (1999) Bioorg. Med. Chem. 7, 2727–2735.
46. Kandimalla et al. (1995) J. Am. Chem. Soc., 117, 6416–6417.
47. Kandimalla et al. (1996) Biochemistry, 35, 15332–15339.
48. Yamana et al. (1995) Tetrahedron Lett., 36, 8427–8430.
49. Cardullo et al. (1988) Proc. Natl. Acad. Sci. USA, 85, 8790–8794.
50. Selvin et al. (1995) Enzymology, 246, 300–334.

SEQUENCE LISTING

```
<160> NUMBER OF SEQ ID NOS: 26

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (1)..(18)
<223> OTHER INFORMATION: /note= "All phosphorothioate internucleotide
      linkages"

<400> SEQUENCE: 1
gcgtgcctcc tcactggc                                                   18

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (1)..(18)
<223> OTHER INFORMATION: /note= "These bases are listed 3'->5' left to
      right."
<221> NAME/KEY: misc_feature
<222> LOCATION: (18)..(19)
<223> OTHER INFORMATION: /note= "5'-5' internucleotide linkage"

<400> SEQUENCE: 2
cggtcactcc tccgtgcggc cagt                                            24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (1)..(18)
<223> OTHER INFORMATION: /note= "These bases are listed 3'->5' left to
      right."
<221> NAME/KEY: misc_feature
<222> LOCATION: (18)..(19)
<223> OTHER INFORMATION: /note= "5'-5' internucleotide linkage"

<400> SEQUENCE: 3
cggtcactcc tccgtgcggc gaat                                            24

<210> SEQ ID NO 4
<211> LENGTH: 24
```

```
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (19)..(24)
<223> OTHER INFORMATION: /note= "These bases are listed 3'->5' left to
      right."
<221> NAME/KEY: misc_feature
<222> LOCATION: (18)..(19)
<223> OTHER INFORMATION: /note=  "3'->3' internucleotide linkage"

<400> SEQUENCE: 4
gcgtgcctcc tcactggccg cacg                                            24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (18)..(23)
<223> OTHER INFORMATION: /note= "These bases are listed 3'->5'left to
      right."
<221> NAME/KEY: misc_feature
<222> LOCATION: (17)..(18)
<223> OTHER INFORMATION: /note= "3'-3' internucleotide linkage"

<400> SEQUENCE: 5
gcgtgcctcc tcacggcgga acc                                             23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (19)..(23)
<223> OTHER INFORMATION: /note= "These bases are listed 3'->5' left to
      right."
<221> NAME/KEY: misc_feature
<222> LOCATION: (18)..(19)
<223> OTHER INFORMATION: /note= "3'-3' internucleotide linkage"
<221> NAME/KEY: misc_feature
<222> LOCATION: (1)..(18)
<223> OTHER INFORMATION: /note= "All phosphorothioate internucleotide
      linkages"

<400> SEQUENCE: 6
gcgtgcctcc tcactggccg cac                                             23

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (19)..(24)
<223> OTHER INFORMATION: /note= "These bases are listed 3'->5' left to
      right."
<221> NAME/KEY: misc_feature
<222> LOCATION: (18)..(19)
```

```
<223> OTHER INFORMATION: /note= "3'-3' internucleotide linkage"
<221> NAME/KEY: misc_feature
<222> LOCATION: (1)..(18)
<223> OTHER INFORMATION: /note= "All phosphorothioate internucleotide
      linkages"

<400> SEQUENCE: 7
gcgtgcctcc tcactggccg cacg                                                 24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (19)..(25)
<223> OTHER INFORMATION: /note= "These bases are listed 3'->5' left to
      right."
<221> NAME/KEY: misc_feature
<222> LOCATION: (18)..(19)
<223> OTHER INFORMATION: /note= "3'-3' internucleotide linkage"
<221> NAME/KEY: misc_feature
<222> LOCATION: (1)..(18)
<223> OTHER INFORMATION: /note= "All phosphorothioate internucleotide
      linkages"

<400> SEQUENCE: 8
gcgtgcctcc tcactggccg cacgg                                                25

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (19)..(26)
<223> OTHER INFORMATION: /note= "These bases are listed 3'->5' left to
      right."
<221> NAME/KEY: misc_feature
<222> LOCATION: (18)..(19)
<223> OTHER INFORMATION: /note= "3'-3' internucleotide linkage"
<221> NAME/KEY: misc_feature
<222> LOCATION: (1)..(18)
<223> OTHER INFORMATION: /note= "All phosphorothioate internucleotide
      linkages"

<400> SEQUENCE: 9
gcgtgcctcc tcactggccg cacgga                                               26

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (19)..(23)
<223> OTHER INFORMATION: /note= "These bases are listed 3'->5' left to
      right."
<221> NAME/KEY: misc_feature
<222> LOCATION: (18)..(19)
<223> OTHER INFORMATION: /note= "3'-3' internucleotide linkage"
<221> NAME/KEY: misc_feature
<222> LOCATION: (1)..(18)
<223> OTHER INFORMATION: /note= "All phosphorothioate internucleotide
``` linkages"

<400> SEQUENCE: 10
gcgtgcctcc tcactggcgg aac                                              23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide that is complementary to the mRNA of regulatory
      subunit of protein kinase A
<221> NAME/KEY: misc_feature
<222> LOCATION: (19)..(25)
<223> OTHER INFORMATION: /note= "These bases are listed 3'->5' left to
      right."
<221> NAME/KEY: misc_feature
<222> LOCATION: (18)..(19)
<223> OTHER INFORMATION: /note= "3'-3' internucleotide linkage"
<221> NAME/KEY: misc_feature
<222> LOCATION: (1)..(18)
<223> OTHER INFORMATION: /note= "All phosphorothioate internucleotide
      linkages"

<400> SEQUENCE: 11
gcgtgcctcc tcactggcgg aacag                                            25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (21)..(26)
<223> OTHER INFORMATION: /note= "These bases are listed 3'->5' left to
      right."
<221> NAME/KEY: misc_feature
<222> LOCATION: (20)..(21)
<223> OTHER INFORMATION: /note= "3'-3' internucleotide linkage"
<221> NAME/KEY: misc_feature
<222> LOCATION: (8)
<223> OTHER INFORMATION: /note= "n represents 5-DABCYL-thymidine"

<400> SEQUENCE: 12
tgacaccngt tctcactcac actgtg                                           26

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (21)..(28)
<223> OTHER INFORMATION: /note= "These bases are listed 3'->5' left to
      right"
<221> NAME/KEY: misc_feature
<222> LOCATION: (20)..(21)
<223> OTHER INFORMATION: /note= "3'-3' internucleotide linkage"
<221> NAME/KEY: misc_feature
<222> LOCATION: (10)
<223> OTHER INFORMATION: /note= "n represents 5-DABCYL-thymidine"

<400> SEQUENCE: 13
tgacacctgn tctcactcac actgtgga                                         28

```
<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (1)..(20)
<223> OTHER INFORMATION: /note= "These bases are listed 3'->5' left to
      right."
<221> NAME/KEY: misc_feature
<222> LOCATION: (20)..(21)
<223> OTHER INFORMATION: /note= "5'-5' internucleotide linkage"
<221> NAME/KEY: misc_feature
<222> LOCATION: (8)
<223> OTHER INFORMATION: /note= "n represents 5-DABCYL-thymidine"

<400> SEQUENCE: 14
cactcacnct tgtccacagt gtgagt                                          26

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (1)..(20)
<223> OTHER INFORMATION: /note= "These bases are listed 3'->5' left to
      right."
<221> NAME/KEY: misc_feature
<222> LOCATION: (20)..(21)
<223> OTHER INFORMATION: /note= "3'-3' internucleotide linkage"
<221> NAME/KEY: misc_feature
<222> LOCATION: (10)
<223> OTHER INFORMATION: /note= "n represents 5-DABCYL- thymidine"

<400> SEQUENCE: 15
cactcactcn tgtccacagt gtgagtga                                        28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA

<400> SEQUENCE: 16
atctgtgagt gagaacaggt gtcacctt                                        28

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA

<400> SEQUENCE: 17
ggacccaggt acatctgtga gtgagaacag gtgtcacctt                           40

<210> SEQ ID NO 18
<211> LENGTH: 26
```

```
<212> TYPE: DNA
<213> ORGANISM: Artificial Sequence
<220> FEATURE:
<223> OTHER INFORMATION: Description of Artificial Sequence: MDM2 mRNA
      forward primer; +311 to +366).

<400> SEQUENCE: 18
acaggaactt ggtagtagtc aatcag                                              26

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: MDM2 mRNA
      reverse primer; +368 to +389.

<400> SEQUENCE: 19
tcaaggtgac acctgttctc ac                                                  22

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: MDM2 mRNA
      probe; +338 to +389.

<400> SEQUENCE: 20
cacagatgta cctgagtccg atgattcct                                           29

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: MDM2 mRNA
      reverse primer-2; +415 to +435.

<400> SEQUENCE: 21
ctcttcctga agctcttgta c                                                   21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA

<400> SEQUENCE: 22
tgacacctgt tctcactcac                                                     20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (19)
<223> OTHER INFORMATION: /note= "n represents 5-DABCYL-thymidine"

<400> SEQUENCE: 23
ggtgacacct gttctcacnc                                                     20
```

-continued

```
<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (18)
<223> OTHER INFORMATION: /note= "n represents 5-DABCYL-thymidine"

<400> SEQUENCE: 24
gtgacacctg ttctcacnca                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (16)
<223> OTHER INFORMATION: /note= "n represents 5-DABCYL-thymidine"

<400> SEQUENCE: 25
gacacctgtt ctcacncaca                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide that is complementary to a portion of the human
      MDM2 mRNA
<221> NAME/KEY: misc_feature
<222> LOCATION: (14)
<223> OTHER INFORMATION: /note= "n represents 5-DABCYL-thymidine"

<400> SEQUENCE: 26
cacctgttct cacncacaga                                                   20
```

We claim:

1. An oligonucleobase comprising a functional segment, a protective segment, and a linker segment, wherein
   a) the functional segment comprises an oligonucleobase of 11 to 75 nucleobases having a terminal end and a linker end;
   b) the protective segment comprises an oligonucleobase of 5 to 30 nucleobases having a terminal end and a linker end and is both complementary to a sequence of about 5 to 30 nucleobases within the functional segment and of polarity opposite to the sequence of about 5 to 30 nucleobases in the functional segment to which it is complementary;
   c) the functional segment and the protective segment are covalently linked at their linker ends to each other through the linker segment, wherein the linker segment is a direct bond, a mono-or oligonucleobase of 2 to 5 nucleobases, or a chemical moiety selected from the group consisting of ethylene glycol, tri(ethylene glycol), tetra(ethylene glycol), penta(ethylene glycol), hexa(ethylene glycol), —NH(CH$_2$)$_n$NH—, wherein n is 2, 3, 4, 5, or 6, and combinations thereof; and
   d) the protective segment and the functional segment form a duplex under selected conditions.

2. The oligonucleobase according to claim 1 wherein N–M 6, the functional segment is complementary to a target oligonucleotides, and a region of at least 6 contiguous nucleobases of the functional segment is single stranded under the selected conditions.

3. The oligonucleobase according to claim 2 wherein the functional segment and the protective segment are oligonucleotides and the linker segment is a direct bond, a mono- or oligonucleotide of 2 to 5 nucleotides, or a chemical moiety selected from the group consisting of ethylene glycol, tri(ethylene glycol), tetra(ethylene glycol), penta (ethylene glycol), hexa(ethylene glycol), —NH(CH$_2$)$_n$NH—, wherein n is 2, 3, 4, 5, or 6, and combinations thereof.

4. The oligonucleobase according to claim 3 wherein the functional segment comprises a sequence of at least four contiguous deoxyribonucleotide phosphodiesters and/or phosphorothioates.

5. The oligonucleobase according to claim 4 further comprising one or more 2'-substituted nucleotides.

6. The oligonucleobase according to claim 5 wherein at least the two terminal nucleotides of the functional segment and/or the protective segment are 2'-substituted nucleotides.

7. The oligonucleobase according to claim 5 wherein the 2'-substituted nucleotides are 2'-O-methyl or 2'-O-methoxyethyl nucleotides.

8. The oligonucleobase according to claim 3 further comprising one or more nucleotides with a modified internucleotide linkage selected from the group consisting of phosphorothioate, phosphorodithioate, $C_1$–$C_6$ alkylphosphonate, $C_1$–$C_6$-alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate, pholpholinol, boranophosphate, morpholino, and sulfone internucleotide linkages.

9. The oligonucleobase according to claim 1 wherein the oligonucleobase is a PNA or an LNA.

10. The oligonucleobase according to claim 1 having attached thereon a chemical moiety selected from the group consisting of lipophilic groups, intercalating agents, biotin, streptavidin, diamines, alkaline phosphatase, horseradish peroxidase, and adamantane.

11. The oligonucleobase according to claim 1 having a Donor and an Acceptor molecule attached thereto, wherein there is an observable difference in a physicochemical property of the Donor and/or Acceptor molecule between a state of the oligonucleobase in which the functional segment and the protective segment form a duplex and a state in which the functional segment and the protective segment do not form a duplex.

12. The oligonucleobase according to claim according to claim 11 wherein the Donor molecule is a FRED, the Acceptor molecule is a FREA, and the physicochemical property is fluorescence.

13. The oligonucleobase according to claim 12, wherein the functional segment comprises an oligonucleobase of from 11 to 75 nucleobases, the functional segment has at least 6 more nucleobases than the protective segment, the functional segment is complementary to a target oligonucleobase, and a region of at least 6 contiguous nucleobases of the functional segment is single stranded under the selected conditions.

14. The oligonucleobase according to claim 13 wherein the functional segment and the protective segment are oligonucleotides and the linker segment is a direct bond, a mono- or oligonucleotide of 2 to 5 nucleotides, or a chemical moiety selected from the group consisting of ethylene glycol, tri(ethylene glycol), tetra(ethylene glycol), penta(ethylene glycol), hexa(ethylene glycol), —NH($CH_2$)$_n$NH—, wherein n is 2, 3, 4, 5, or 6, and combinations thereof.

15. The oligonucleobase according to claim 14 wherein the functional segment comprises a sequence of at least four contiguous deoxyribonucleotide phosphodiesters and/or phosphorothioates.

16. The oligonucleobase according to claim 15 further comprising one or more 2'-substituted nucleotides.

17. The oligonucleobase according to claim 16 wherein at least the two terminal nucleotides of the functional segment and/or the protective segment are 2'-substituted nucleotides.

18. The oligonucleobase according to claim 16 wherein the 2'-substituted nucleotides are 2'-O-methyl or 2'-O-methoxyethyl nucleotides.

19. The oligonucleobase according to claim 14 further comprising one or more nucleotides with a modified internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate, pholpholinol, boranophosphate, morpholino, and sulfone internucleotide linkages.

20. The oligonucleobase according to claim 12 wherein the oligonucleobase is a PNA or LNA.

21. The oligonucleobase according to claim 12 having attached thereon a chemical moiety selected from the group consisting of lipophilic groups, intercalating agents, biotin, streptavidin, diamines, alkaline phosphatase, horseradish peroxidase, and adamantane.

22. The oligonucleobase according to claim 1, 11, or 12 wherein the functional segment is a ribozyme.

23. The oligonucleobase according to claim 1, 11, or 12 wherein the functional segment is an aptamer.

24. The oligonucleobase according to any one of claims 1, 3, 11, 12, and 14 wherein the oligonucleobase is adapted for linkage to a solid, surface.

25. The oligonucleobase according to any one of claims 1, 3, 11, 12, and 14 wherein the oligonucleobase is linked to a solid surface.

26. A kit comprising in one or more containers an oligonucleobase according to any one of claims 1, 3, 11, 12, and 14.

27. A kit comprising in one or more containers an oligonucleobase according to claim 24.

28. A kit comprising in one or more containers an oligonucleobase according to claim 25.

29. A method for cleaving an mRNA molecule comprising contacting the mRNA molecule with an oligonucleobase according to any one of claims 2–10 in the presence of an RNase H under conditions that permit hybridization of the functional segment to at least a portion of the RNase H and subsequent cleavage of the mRNA, wherein the functional segment of the oligonucleobase is complementary to at least a portion of the mRNA.

30. A method of detecting a target oligonucleobase comprising contacting the target oligonucleobase with an oligonucleobase according to any one of claims 11–21, wherein the functional segment of the oligonucleobase is complementary to at least a portion of the target oligonucleobase.

31. A method of detecting a target oligonucleobase comprising contacting the target oligonucleobase with an oligonucleobase according to claim 25.

32. In a method of amplifying a target nucleic acid, the improvement comprising using an oligonucleobase according to any one of claims 11–21 as a primer and/or primer-probe, wherein the functional segment is complementary to the target nucleic acid to be amplified.

33. In a method of amplifying a target nucleic acid, the improvement comprising using an oligonucleobase according to claim 25 as a primer and/or primer-probe, wherein the functional segment is complementary to the target nucleic acid to be amplified.

* * * * *

UNITED STATES PATENT AND TRADEMARK OFFICE
CERTIFICATE OF CORRECTION

PATENT NO. : 6,383,752 B1
DATED : May 7, 2002
INVENTOR(S) : Agrawal et al.

It is certified that error appears in the above-identified patent and that said Letters Patent is hereby corrected as shown below:

<u>Column 40,</u>
Line 50, please delete the phrase "N-M 6," and insert in its place the phrase -- the functional segment has at least 6 more nucleobases than the protective segment, --.

<u>Column 41,</u>
Line 11, please delete the dash (-) after the phrase "$C_1$-$C_6$" and replace it with a space.
Line 33, please delete the phrase "to claim according".

<u>Column 42,</u>
Line 25, please delete the comma after the word "solid".

Signed and Sealed this

Sixth Day of August, 2002

Attest:

Attesting Officer

JAMES E. ROGAN
*Director of the United States Patent and Trademark Office*